(12) United States Patent
Dimaio et al.

(10) Patent No.: US 12,162,143 B2
(45) Date of Patent: Dec. 10, 2024

(54) SYSTEMS AND METHODS FOR MASTER/TOOL REGISTRATION AND CONTROL FOR INTUITIVE MOTION

(71) Applicant: INTUITIVE SURGICAL OPERATIONS, INC., Sunnyvale, CA (US)

(72) Inventors: Simon P. Dimaio, San Carlos, CA (US); Ambarish G. Goswami, Fremont, CA (US); Dinesh Rabindran, San Jose, CA (US); Changyeob Shin, Los Angeles, CA (US); Tao Zhao, Sunnyvale, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 0 days.

(21) Appl. No.: 18/409,350

(22) Filed: Jan. 10, 2024

(65) Prior Publication Data
US 2024/0139936 A1 May 2, 2024

Related U.S. Application Data

(63) Continuation of application No. 17/287,430, filed as application No. PCT/US2019/056443 on Oct. 16, 2019, now Pat. No. 11,897,127.
(Continued)

(51) Int. Cl.
*B25J 9/02* (2006.01)
*B25J 9/00* (2006.01)
(Continued)

(52) U.S. Cl.
CPC ............... *B25J 9/02* (2013.01); *B25J 9/0084* (2013.01); *B25J 9/1697* (2013.01); *B25J 15/0071* (2013.01)

(58) Field of Classification Search
CPC . B25J 9/02; B25J 9/0084; B25J 9/1697; B25J 15/0071; A61B 34/25;
(Continued)

(56) References Cited

U.S. PATENT DOCUMENTS

| | | | |
|---|---|---|---|
| 5,560,360 | A | 10/1996 | Filler et al. |
| 6,044,308 | A | 3/2000 | Huissoon |

(Continued)

FOREIGN PATENT DOCUMENTS

| | | |
|---|---|---|
| CN | 103188987 A | 7/2013 |
| CN | 105078580 A | 11/2015 |

(Continued)

OTHER PUBLICATIONS

Allan M., et al., "Image Based Surgical Instrument Pose Estimation with Multi-class Labelling and Optical Flow," International Conference on Financial Cryptography and Data Security, Nov. 18, 2015, pp. 331-338.
(Continued)

*Primary Examiner* — Jaime Figueroa
(74) *Attorney, Agent, or Firm* — Haynes & Boone, LLP.

(57) ABSTRACT

A method is performed by a computing system. The method includes receiving image data from an imaging device, and determining, using the image data, a plurality of image-space tools, each image-space tool associated with a tool of a plurality of tools, each tool controlled by a manipulator of a plurality of manipulators. The method further includes determining a first correspondence between a first image-space tool of the plurality of image-space tools and a first tool of the plurality of tools based on a first disambiguation setting associated with the first tool.

20 Claims, 13 Drawing Sheets

Related U.S. Application Data

(60) Provisional application No. 62/748,698, filed on Oct. 22, 2018.

(51) Int. Cl.
  *B25J 9/16* (2006.01)
  *B25J 15/00* (2006.01)

(58) Field of Classification Search
  CPC .... A61B 2034/2048; A61B 2034/2051; A61B 2034/2055; A61B 34/20; A61B 34/74; A61B 34/76; A61B 90/361; A61B 90/37; A61B 90/90
  See application file for complete search history.

(56) References Cited

U.S. PATENT DOCUMENTS

| | | | |
|---|---|---|---|
| 6,165,170 A | 12/2000 | Wynne et al. | |
| 6,671,581 B2 | 12/2003 | Niemeyer et al. | |
| 6,711,433 B1 | 3/2004 | Geiger et al. | |
| 6,837,883 B2 | 1/2005 | Moll et al. | |
| 6,941,513 B2 | 9/2005 | Meystel et al. | |
| 7,010,390 B2 | 3/2006 | Graf et al. | |
| 8,073,528 B2 | 12/2011 | Zhao et al. | |
| 8,108,072 B2 | 1/2012 | Zhao et al. | |
| 8,147,503 B2 | 4/2012 | Zhao et al. | |
| 8,781,630 B2* | 7/2014 | Banks | A61B 6/12 378/197 |
| 8,792,963 B2 | 7/2014 | Zhao et al. | |
| 9,259,289 B2 | 2/2016 | Zhao et al. | |
| 9,782,229 B2* | 10/2017 | Crawford | A61B 10/0233 |
| 9,827,057 B2 | 11/2017 | Zhao et al. | |
| 10,485,617 B2* | 11/2019 | Crawford | A61B 17/1671 |
| 10,522,145 B2 | 12/2019 | Ogawa | |
| 10,675,094 B2* | 6/2020 | Crawford | A61B 34/71 |
| 10,758,315 B2* | 9/2020 | Johnson | A61B 90/98 |
| 10,828,104 B2 | 11/2020 | Jagga et al. | |
| 10,835,326 B2* | 11/2020 | Crawford | A61N 1/0529 |
| 10,842,461 B2* | 11/2020 | Johnson | A61B 34/20 |
| 11,071,594 B2* | 7/2021 | Kostrzewski | A61B 17/1703 |
| 11,116,576 B2* | 9/2021 | Theodore | A61B 34/20 |
| 11,135,015 B2* | 10/2021 | Crawford | A61B 34/20 |
| 11,253,320 B2* | 2/2022 | Crawford | A61B 34/30 |
| 11,395,706 B2* | 7/2022 | Joshi | A61B 90/90 |
| 11,464,573 B1 | 10/2022 | Roh et al. | |
| 11,771,499 B2* | 10/2023 | Crawford | A61B 90/37 606/279 |
| 2005/0107920 A1 | 5/2005 | Ban et al. | |
| 2006/0258938 A1 | 11/2006 | Hoffman et al. | |
| 2008/0091634 A1 | 4/2008 | Seeman | |
| 2008/0161684 A1 | 7/2008 | Li et al. | |
| 2008/0192996 A1 | 8/2008 | Timmer et al. | |
| 2011/0276179 A1* | 11/2011 | Banks | A61B 34/76 700/264 |
| 2011/0320039 A1 | 12/2011 | Hsu et al. | |
| 2014/0100694 A1 | 4/2014 | Rueckl et al. | |
| 2014/0275997 A1 | 9/2014 | Chopra et al. | |
| 2016/0023355 A1 | 1/2016 | Komatsu et al. | |
| 2016/0030117 A1 | 2/2016 | Mewes | |
| 2016/0346930 A1 | 12/2016 | Hares | |
| 2021/0153940 A1 | 5/2021 | Jagga et al. | |
| 2021/0354286 A1 | 11/2021 | Dimaio et al. | |

FOREIGN PATENT DOCUMENTS

| | | | |
|---|---|---|---|
| WO | WO-2010147729 A1 | 12/2010 | |
| WO | WO-2013023130 A1 | 2/2013 | |
| WO | WO-2014146085 A1 | 9/2014 | |
| WO | WO-2014146090 A1 | 9/2014 | |
| WO | WO-2016069655 A1 | 5/2016 | |
| WO | WO-2019099346 A2 | 5/2019 | |
| WO | WO-2019103954 A1 | 5/2019 | |

OTHER PUBLICATIONS

International Preliminary Report on Patentability for Application No. PCT/US2019/056443, mailed on May 6, 2021, 13 pages.

International Search Report and Written Opinion for Application No. PCT/US2019/056443, mailed on Apr. 6, 2020, 21 pages.

Invitation to pay additional fee received from the International Search Authority for PCT/US2019/056443, mailed Feb. 10, 2020, 17 pages.

Pachtrachai K., et al., "Hand-eye Calibration for Robotic Assisted Minimally Invasive Surgery Without a Calibration Object", IEEE/RSJ International Conference on Intelligent Robots and Systems (IROS), Oct. 9, 2016, pp. 2485-2491.

Vertut, J., and Coiffet, P., "Robot Technology: Teleoperation and Robotics Evolution and Development," English translation, Prentice-Hall, Inc., Inglewood Cliffs, NJ, USA 1986, vol. 3A, 332 pages.

Wu L., et al., "Finding the Kinematic Base Frame of a Robot by Hand-Eye Calibration Using 3D Position Data," IEEE Transactions on Automation Science and Engineering, Jan. 2017, vol. 14 (1), pp. 314-324.

\* cited by examiner

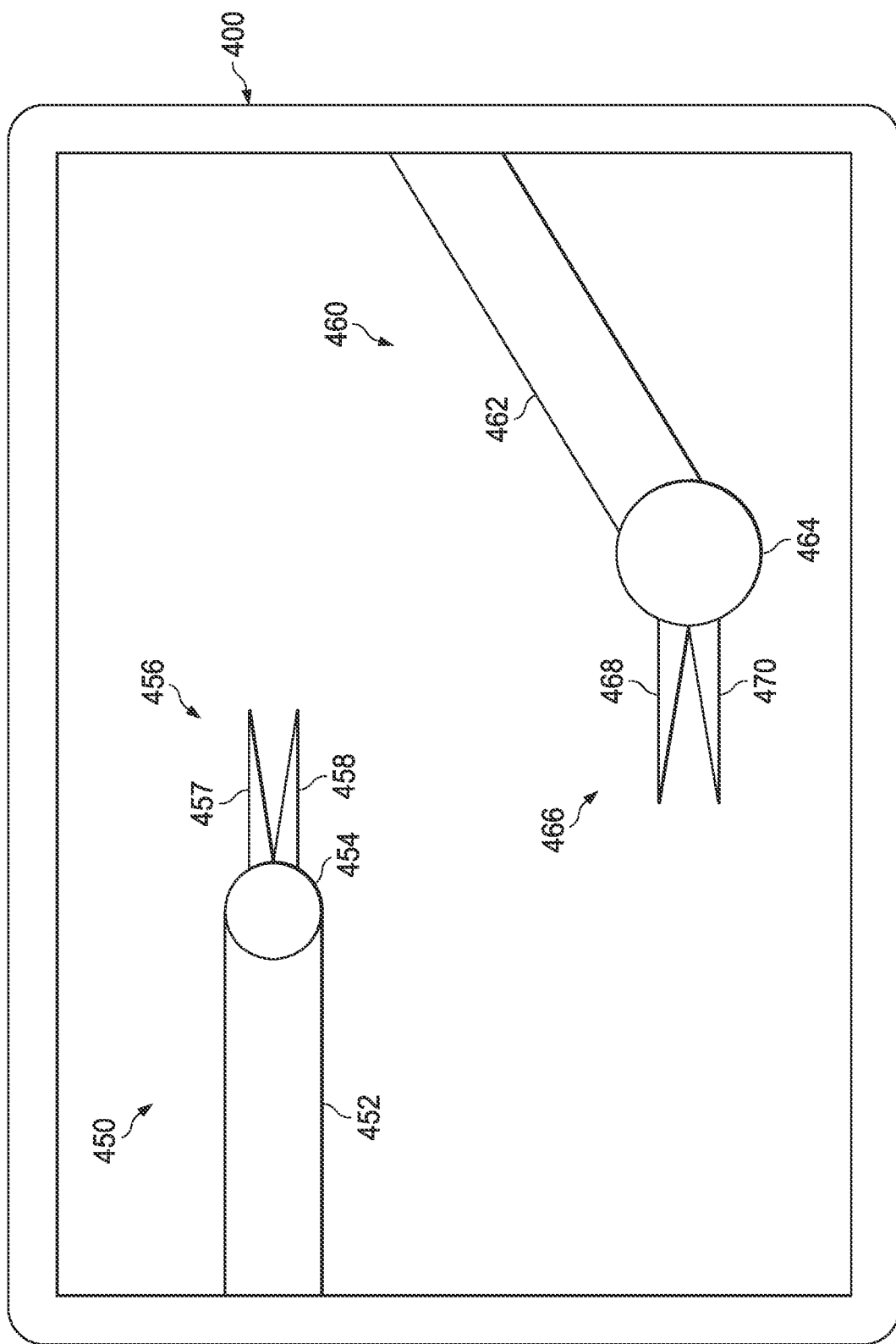

SYSTEMS AND METHODS FOR MASTER/TOOL REGISTRATION AND CONTROL FOR INTUITIVE MOTION

CROSS-REFERENCE TO RELATED APPLICATIONS

This application is a continuation of U.S. patent application Ser. No. 17/287,430, filed Apr. 21, 2021, which is the U.S. national phase of International Application No. PCT/US2019/056443, filed Oct. 16, 2019, which designates the U.S. and claims priority to and the benefit of U.S. Provisional Application 62/748,698 filed Oct. 22, 2018, both of which are incorporated by reference herein in their entirety.

FIELD

The present disclosure is directed to systems and methods for performing a robotic procedure, and more particularly to systems and methods for determining master-to-tool alignments used in controlling the movement of tools.

BACKGROUND

A system of robotic devices can be used to perform a task at a worksite. For example, robotic systems can include robotic manipulators to manipulate instruments for performing the task. The robotic manipulator can include two or more links coupled together by one or more joints. The joints can be active joints that are actively controlled. The joints can also be passive joints that comply with movement of the active joints as the active joints are actively controlled. Such active and passive joints may be revolute or prismatic joints. The configuration of the robotic manipulator may then be determined by the positions and orientations of the joints, the structure of the robotic manipulator, and the coupling of the links.

Robotic systems include industrial and recreational robotic systems. Robotic systems also include medical robotic systems used in procedures for diagnosis, non-surgical treatment, surgical treatment, etc. As a specific example, robotic systems include minimally invasive, robotic telesurgical systems in which a surgeon can operate on a patient from bedside or a remote location. Telesurgery refers generally to surgery performed using surgical systems where the surgeon uses some form of remote control, e.g., a servomechanism, to manipulate surgical instrument movements rather than directly holding and moving the instruments by hand. A robotic medical system usable for telesurgery or other telemedical procedures can include a remotely controllable robotic manipulator. Operators can remotely control motion of the remotely controllable robotic manipulator. Operators can also manually move pieces of the robotic medical system into positions or orientations within its environment.

In the robotic systems, various applications may depend on accurate correspondences between the tools and the image-space tools in images of the work site (e.g., provided by an imaging device controlled by a robotic manipulator or a human manipulator). Such applications may include, for example, a graphical information display system that overlays graphic information of the manipulators and their tools to the corresponding image-space tools in a display, an autonomous task execution system heavily guided by machine vision of the work site. For further example, in robotic telesurgical systems used in a surgical environment, multiple image-guided tools may be inserted into the patient anatomy, and images of the patient anatomy including the multiple image-space tools may be used to guide the medical operation. However, in embodiments where a robotic system includes multiple tools, ambiguity in establishing the correspondence of multiple tools to multiple image-space tools in the images may arise, which may affect the performance (e.g., content accuracy of the graphical information display system, intuitiveness of the robotic telesurgical systems) of those applications depending on the correspondence of multiple tools to multiple image-space tools of the instruments may arise, which may affect the intuitiveness of a teleoperational system.

Accordingly, it would be advantageous to provide an improved disambiguation process for establishing instrument and image correspondences.

SUMMARY

The embodiments of the invention are summarized by the claims that follow below.

In some embodiments, a robotic system includes a plurality of manipulators configured to physically couple to a plurality of tools and a control system communicatively coupled to the plurality of manipulators. The control system is configured to receive image data provided by an imaging device, and determine, based on the image data, a plurality of image-space tools. Each image-space tool is associated with a tool of a plurality of tools. The control system is further configured to determine a first correspondence between a first image-space tool of the plurality of image-space tools and a first tool of the plurality of tools based on a first disambiguation setting associated with the first tool.

In some embodiments, a method is performed by a computing system. The method includes receiving image data provided by an imaging device and determining, using the image data, a plurality of image-space tools, each image-space tool associated with a tool of a plurality of tools. Each tool is controlled by a manipulator of a plurality of manipulators. The method further includes determining a first correspondence between a first image-space tool of the plurality of image-space tools and a first tool of the plurality of tools based on a first disambiguation setting associated with the first tool.

In some embodiments, a non-transitory machine-readable medium includes a plurality of machine-readable instructions which, when executed by one or more processors, are adapted to cause the one or more processors to perform a method. The method includes receiving image data from an imaging device, and determining, using the image data, a plurality of image-space tools, each image-space tool associated with a tool of a plurality of tools, each tool controlled by a manipulator of a plurality of manipulators. The method further includes determining a first correspondence between a first image-space tool of the plurality of image-space tools and a first tool of the plurality of tools based on a first disambiguation setting associated with the first tool.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTIONS OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. In addition, the present disclosure may repeat reference numerals and/or letters in the various examples. This repetition is for the purpose of simplicity and clarity and does not in itself dictate a relationship between the various embodiments and/or configurations discussed.

FIG. 4B is another imaging view through a display of an operator's control console in accordance with an embodiment of the present disclosure.

DETAILED DESCRIPTION

Figure 1A:
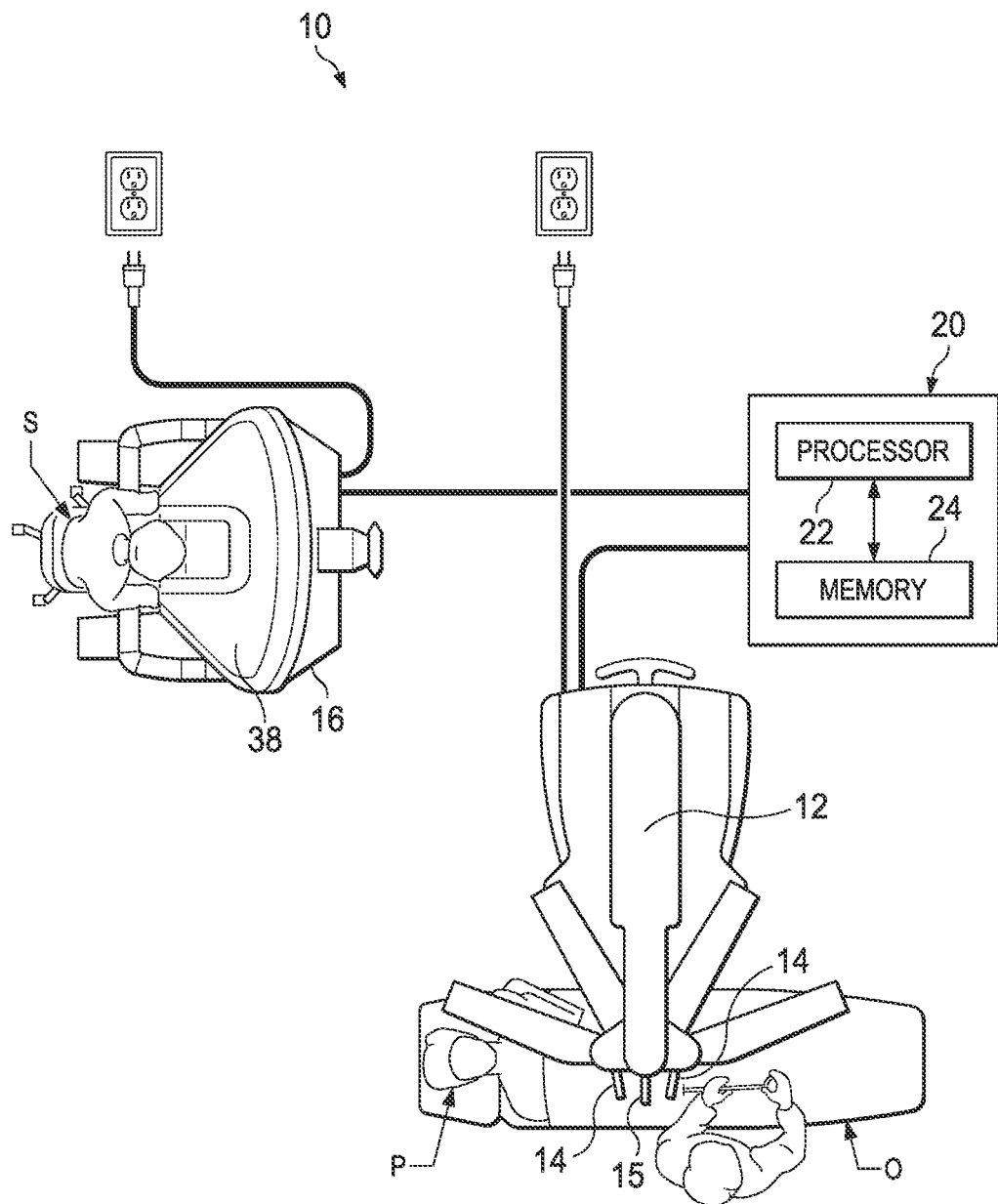
FIG. 1A is a schematic view of a robotic medical system, in accordance with an embodiment of the present disclosure.

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. In the following detailed description of the aspects of the invention, numerous specific details are set forth in order to provide a thorough understanding of the disclosed embodiments. However, it will be obvious to one skilled in the art that the embodiments of this disclosure may be practiced without these specific details. In other instances, well-known methods, procedures, components, and circuits have not been described in detail so as not to unnecessarily obscure aspects of the embodiments of the invention.

Any alterations and further modifications to the described devices, tools, methods, and any further application of the principles of the present disclosure are fully contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. In addition, dimensions provided herein are for specific examples and it is contemplated that different sizes, dimensions, and/or ratios may be utilized to implement the concepts of the present disclosure. To avoid needless descriptive repetition, one or more components or actions described in accordance with one illustrative embodiment can be used or omitted as applicable from other illustrative embodiments. For the sake of brevity, the numerous iterations of these combinations will not be described separately. For simplicity, in some instances, the same reference numbers are used throughout the drawings to refer to the same or like parts.

Although some of the examples described herein refer to surgical procedures or tools, or medical procedures and medical tools, the techniques disclosed apply to medical and non-medical procedures, and to medical and non-medical tools. For example, the tools, systems, and methods described herein may be used for non-medical purposes including industrial uses, general robotic uses, and sensing or manipulating non-tissue work pieces. Other example applications involve cosmetic improvements, imaging of human or animal anatomy, gathering data from human or animal anatomy, setting up or taking down the system, and training medical or non-medical personnel. Additional example applications include use for procedures on tissue removed from human or animal anatomies (without return to a human or animal anatomy), and performing procedures on human or animal cadavers. Further, these techniques can also be used for medical treatment or diagnosis procedures that do, or do not, include surgical aspects.

The embodiments below will describe various tools and portions of tools in terms of their state in three-dimensional space. As used herein, the term "position" refers to the location of an object or a portion of an object in a three-dimensional space (e.g., three degrees of translational freedom that can be described using changes in Cartesian X, Y, Z coordinates, such as along Cartesian X, Y, Z axes). As used herein, the term "orientation" refers to the rotational placement of an object or a portion of an object (three degrees of rotational freedom—e.g., which can be described using roll, pitch, and yaw). As used herein, the term "pose" of an object, or a portion of an object, refers to the position and orientation of the object or the portion of the object. Pose information may comprise position data in at least one degree of translational freedom, orientation data in at least one degree of rotational freedom, or both position and orientation data. For example, for a rigid body in a three-dimensional space, a full pose can be described with pose data comprising six parameters in six total degrees of freedom (e.g. three translational for position, and three rotational for orientation). As another example, a partial pose can be described with pose data comprising fewer than six parameters, and describing only the position, describing only the orientation, or describing both position and orientation but to less than a full pose.

Referring to FIG. 1A of the drawings, an example robotic system is shown. Specifically, in FIG. 1A, a computer-aided, robotic medical system that may be teleoperated and used in, for example, medical procedures including diagnostic, therapeutic, or surgical procedures, is generally indicated by the reference numeral 10. As will be described, the teleoperational systems of this disclosure are under the teleoperational control of an operator. In some embodiments, manipulators or other parts of a robotic system may be controlled directly through manual interaction with the manipulators (or the other parts) themselves. Thus, "teleoperated manipulators" as used in this application include manipulators that can be controlled only through teleoperation, and manipulators that can be controlled through teleoperation and through direct manual control. Further, in some embodiments, a non-teleoperational or robotic medical system may be under the partial control of a computer programmed to perform the procedure or sub-procedure. In still other alternative embodiments, a fully automated medical system, under the full control of a computer programmed to perform the procedure or sub-procedure, may be used to perform procedures or sub-procedures.

As shown in FIG. 1A, the robotic medical system 10 generally includes a manipulator assembly 12 mounted to or near an operating table O on which a patient P is positioned. The manipulator assemblies described herein often include one or more robotic manipulators and tools mounted thereon, although the term "manipulator assembly" also encompasses the manipulator without the tool mounted thereon. The manipulator assembly 12 may be referred to as a patient side cart in this example, since it comprises a cart and is designed to be used next to a patient. A medical tool 14 (also referred to as a tool 14) and a medical tool 15 are operably coupled to the manipulator assembly 12. Within this disclosure, the medical tool 15 includes an imaging device, and may also be referred to as the imaging tool 15. The imaging tool 15 may comprise an endoscopic imaging system using optical imaging technology, or comprise another type of imaging system using other technology (e.g. ultrasonic, fluoroscopic, etc.). An operator input system 16 allows an operator such as a surgeon or other type of clinician S to view images of or representing the procedure site and to control the operation of the medical tool 14 and/or the imaging tool 15.

As shown in FIG. 1A, the operator input system 16 is connected to an operator's console 38 that is usually located in the same room as operating table O during a surgical procedure. It should be understood, however, that the operator S can be located in a different room or a completely different building from the patient P. The operator input system 16 generally includes one or more control device(s) for controlling the medical tool 14. The operator input system 16 is also referred to herein as "master input devices," and "input devices." The control device(s) may include one or more of any number of a variety of input devices, such as hand grips, joysticks, trackballs, data gloves, trigger-guns, foot pedals, hand-operated controllers, voice recognition devices, touch screens, body motion or presence sensors, and the like. In some embodiments, the control device(s) will be provided with the same degrees of freedom as the medical tools of the robotic assembly to provide the operator with telepresence; that is, the operator is provided with the perception that the control device(s) are integral with the tools so that the operator has a sense of directly controlling tools as if present at the procedure site. In other embodiments, the control device(s) may have more or fewer degrees of freedom than the associated medical tools and still provide the operator with telepresence. In some embodiments, the control device(s) are manual input devices which move with six degrees of freedom, and which may also include an actuatable handle for actuating medical tools (for example, for closing grasping jaw end effectors, applying an electrical potential to an electrode, capture images, delivering a medicinal treatment, and the like).

The manipulator assembly 12 supports and manipulates the medical tool 14 while the operator S views the procedure site through the operator's console. An image of the procedure site can be obtained by the medical tool 15, such as via an imaging system comprising a monoscopic or stereoscopic endoscope, which can be manipulated by the manipulator assembly 12 to orient the medical tool 15. An electronics cart can be used to process the images of the procedure site for subsequent display to the operator S through the operator's console. The number of medical tools 14 used at one time will generally depend on the medical diagnostic or treatment (e.g. surgical) procedure and the space constraints within the operating environment, among other factors. The manipulator assembly 12 may include a kinematic structure of one or more non-servo controlled links (e.g., one or more links that may be manually positioned and locked in place) and a robotic manipulator. The manipulator assembly 12 includes a plurality of motors that drive inputs on the medical tools 14. These motors move in response to commands from the control system (e.g., control system 20). The motors include drive systems which when coupled to the medical tools 14 may advance the medical instrument into a naturally or surgically created anatomical orifice. Other motorized drive systems may move the distal end of the medical instrument in multiple degrees of freedom, which may include three degrees of linear motion (e.g., linear motion along the X, Y, Z Cartesian axes) and in three degrees of rotational motion (e.g., rotation about the X, Y, Z Cartesian axes). Additionally, the motors can be used to actuate an articulable end effector of the tool for grasping tissue in the jaws of a biopsy device or the like. The medical tools 14 may include end effectors having a single working member such as a scalpel, a blunt blade, a needle, an imaging sensor, an optical fiber, an electrode, etc. Other end effectors may include multiple working members, and examples include forceps, graspers, scissors, clip appliers, staplers, bipolar electrocautery instruments, etc.

The robotic medical system 10 also includes a control system 20. The control system 20 includes at least one memory 24 and at least one processor 22, and typically a plurality of processors, for effecting control between the medical tool 14, the operator input system 16, and other auxiliary systems 26 which may include, for example, imaging systems, audio systems, fluid delivery systems, display systems, illumination systems, steering control systems, irrigation systems, and/or suction systems. The control system 20 also includes programmed instructions (e.g., a computer-readable medium storing the instructions) to implement some or all of the methods described in accordance with aspects disclosed herein. While control system 20 is shown as a single block in the simplified schematic of FIG. 1A, the system may include two or more data processing circuits with one portion of the processing optionally being performed on or adjacent the manipulator assembly 12, another portion of the processing being performed at the operator input system 16, and the like. Any of a wide variety of centralized or distributed data processing architectures may be employed. Similarly, the programmed instructions may be implemented as a number of separate programs or subroutines, or they may be integrated into a number of other aspects of the teleoperational systems described herein. In one embodiment, control system 20 supports wireless communication protocols such as Bluetooth, IrDA, HomeRF, IEEE 802.11, DECT, and Wireless Telemetry.

In some embodiments, the control system 20 may include one or more servo controllers that receive force and/or torque feedback from the medical tool 14 or from the manipulator assembly 12. Responsive to the feedback, the servo controllers transmit signals to the operator input system 16. The servo controller(s) may also transmit signals that instruct the manipulator assembly 12 to move the medical tool(s) 14 and/or 15 which extends into an internal procedure site within the patient body via openings in the body. Any suitable conventional or specialized controller may be used. A controller may be separate from, or integrated with, manipulator assembly 12. In some embodiments, the controller and manipulator assembly are provided as part of an integrated system such as a teleoperational arm cart positioned proximate to the patient's body during the medical procedure.

The control system 20 can be coupled to the medical tool 15 and can include a processor to process captured images for subsequent display, such as to an operator using the operator's console or wearing a head-mounted display system, on one or more stationary or movable monitors near the control system, or on another suitable display located locally and/or remotely. For example, where a stereoscopic endoscope is used, the control system 20 can process the captured images to present the operator with coordinated stereo images of the procedure site. Such coordination can include alignment between the stereo images and can include adjusting the stereo working distance of the stereoscopic endoscope.

In alternative embodiments, the robotic system may include more than one manipulator assembly and/or more than one operator input system. The exact number of manipulator assemblies will depend on the surgical procedure and the space constraints for the robotic system, among other factors. The operator input systems may be collocated, or they may be positioned in separate locations. Multiple operator input systems allow more than one operator to control one or more manipulator assemblies in various combinations.

Figure 1B:
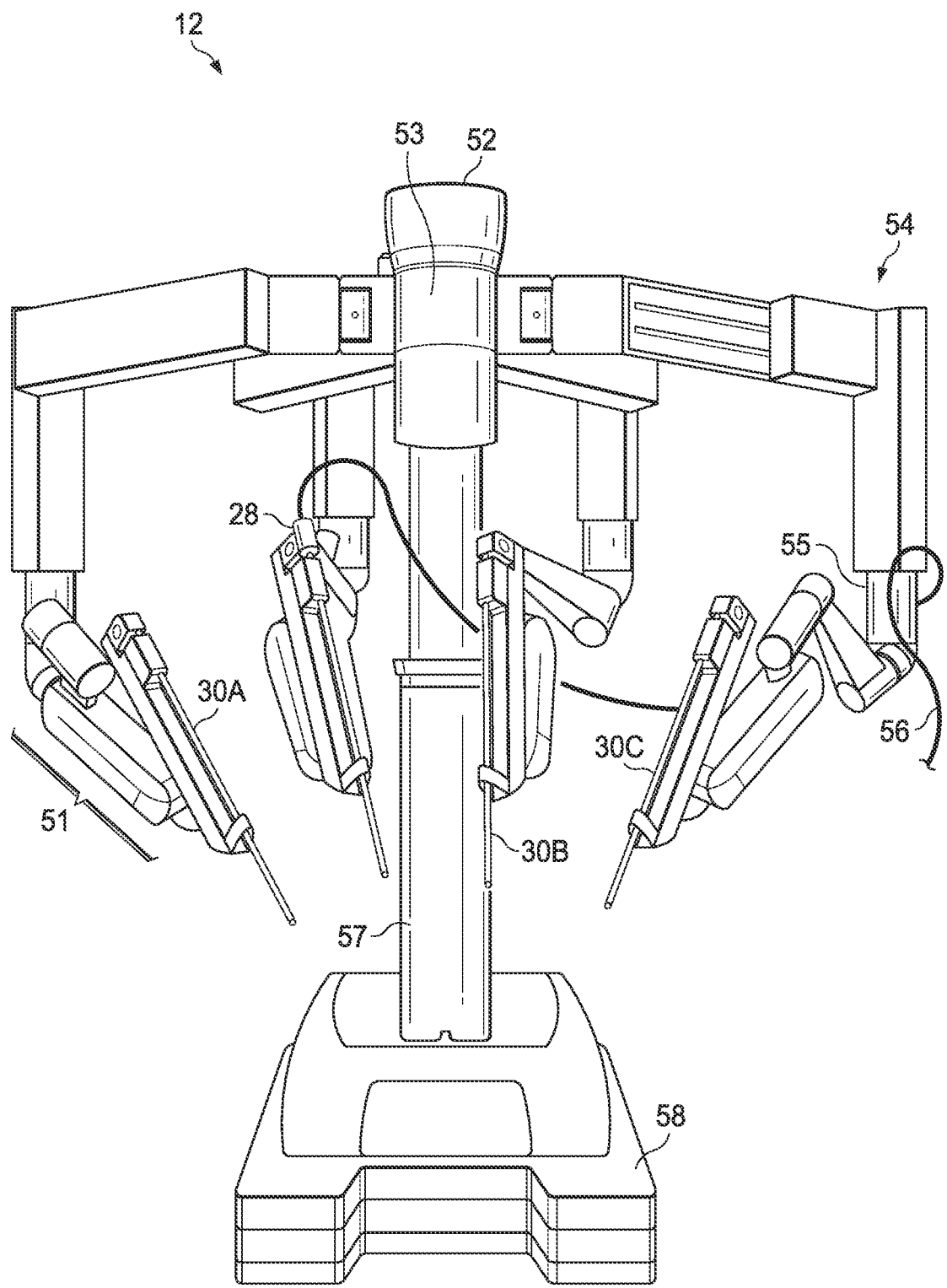
FIG. 1B is a perspective view of a manipulator assembly, in accordance with an embodiment of the present disclosure.

FIG. 1B is a perspective view of one embodiment of a manipulator assembly 12 that is configured in the form of a cart that is located near the patient during a medical procedure. Thus, this manipulator assembly of FIG. 1B may also be referred to as a patient side cart. The manipulator assembly 12 shown provides for the manipulation of three medical tools 30a, 30b, 30c (e.g., medical tools 14) and a medical tool 28 including an imaging device (e.g., medical tool 15), such as a stereoscopic endoscope used for the capture of images of the workpiece or of the site of the procedure (also called "work site"). The medical tool 28 may transmit signals over a cable 56 to the control system 20. Manipulation is provided by robotic manipulators having a number of joints. The medical tool 28 and the surgical tools 30a-c can be positioned and manipulated through incisions in, or natural orifices of, the patient so that a kinematic remote center is maintained at the incisions or natural orifices. Images of the work site can include images of the distal ends of the surgical tools 30a-c when they are positioned within the field-of-view of the imaging device of the medical tool 28.

The manipulator assembly 12 includes a movable, lockable, and drivable base 58. The base 58 is connected to a telescoping column 57, which allows for adjustment of the height of the arms 54 (also called "manipulators 54"). The arms 54 may include a rotating joint 55 that both rotates and translates parallel to the column 57. The arms 54 may be connected to an orienting platform 53. The orienting platform 53 may be capable of 360 degrees of rotation. The manipulator assembly 12 may also include a telescoping horizontal cantilever 52 for moving the orienting platform 53 in a horizontal direction.

In the present example, each of the arms 54 includes a manipulator arm portion 51. The manipulator arm portion 51 may connect directly to a medical tool 14. The manipulator arm portion 51 may be teleoperatable. In some examples, the arms 54 connecting to the orienting platform are not teleoperatable. Rather, such arms 54 are positioned as desired before the operator S begins operation with the teleoperative components.

Endoscopic and other imaging systems (e.g., medical tools 15, 28) may be provided in a variety of configurations, including ones having rigid or flexible structures, and ones that are articulatable or non-articulatable. Rigid endoscopes include a rigid tube housing a relay lens system for transmitting an image from a distal end to a proximal end of the endoscope. Flexible endoscopes transmit images using one or more flexible optical fibers. Digital image based endoscopes may have a "chip on the tip" design in which a distal digital sensor such as a one or more charge-coupled device (CCD) or a complementary metal oxide semiconductor (CMOS) device store image data. Endoscopic imaging systems may also utilize other imaging techniques such as ultrasonic, infrared, and fluoroscopic technologies. Endoscopic imaging systems may provide two- or three-dimensional images to the viewer. Two-dimensional images may provide limited depth perception. Three-dimensional stereo endoscopic images may provide the viewer with more accurate depth perception. Stereo endoscopic tools employ stereo cameras to capture stereo images of the patient anatomy. An endoscopic tool may be a fully sterilizable assembly with the endoscope cable, handle and shaft all rigidly coupled and hermetically sealed.

Figure 1C:
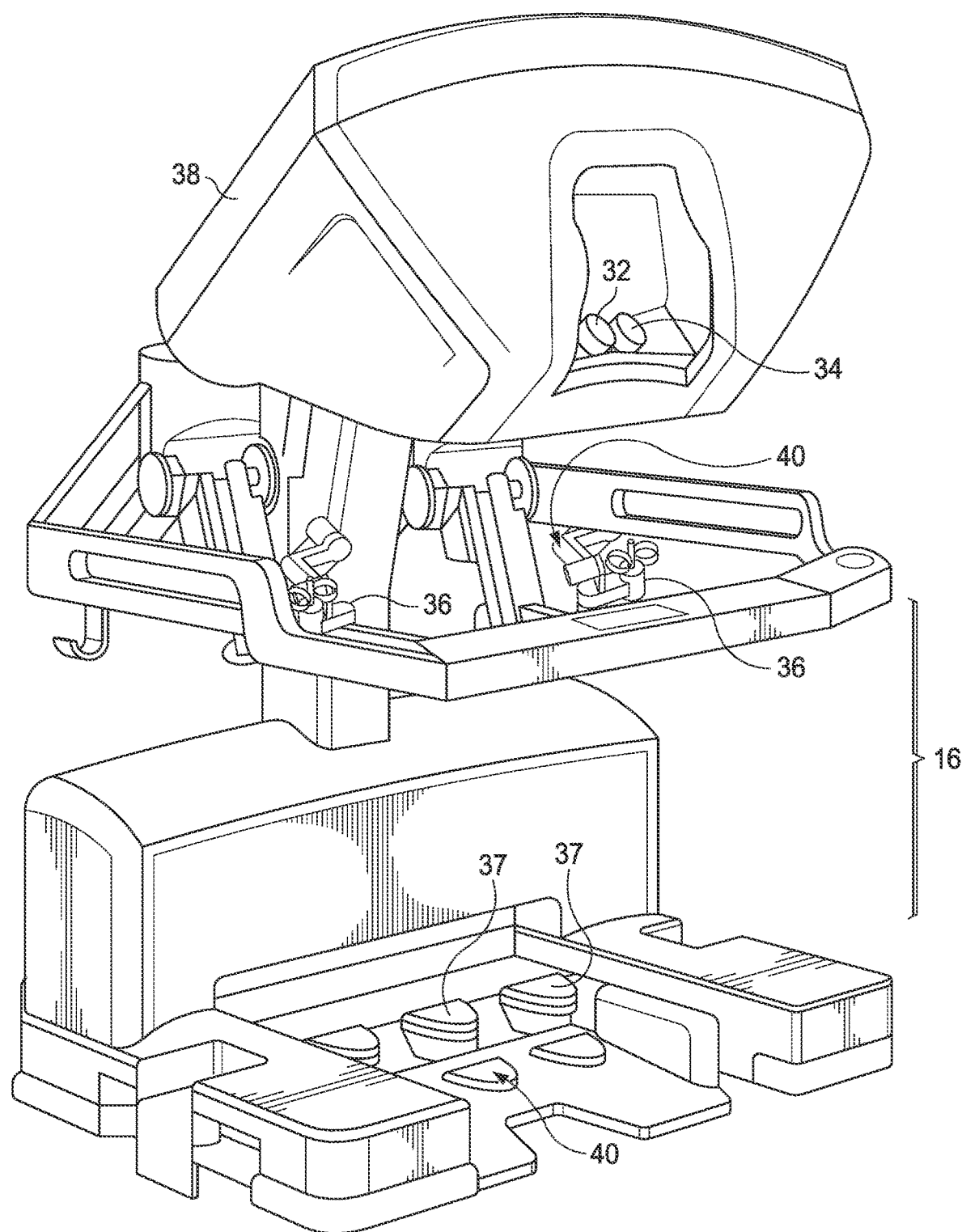
FIG. 1C is a perspective view of an operator's control console for a robotic medical system, in accordance with an embodiment of the present disclosure.

FIG. 1C is a perspective view of the operator's console 38. The operator's console 38 includes a left eye display 32 and a right eye display 34 for presenting the operator S with a coordinated stereo view of the surgical environment that enables depth perception. An operator input system 16 of the operator's console 38 includes one or more input control devices 36, which in turn causes the manipulator assembly 12 to manipulate one or more medical tools (e.g., medical tools 14, 15, 28, 30a-c). The input control devices 36 may be used to, for example, close grasping jaw end effectors, apply an electrical potential to an electrode, deliver a medicinal treatment, or the like. In various alternatives, the input control devices 36 may additionally or alternatively include joystick devices, trackballs, data gloves, trigger-guns, hand-operated controllers, voice recognition devices, touch screens, body motion or presence sensors, and the like. In some embodiments and for some associated medical tools 14, the input control devices 36 will provide the same degrees of freedom as their associated medical tools 14 to provide the operator S with telepresence, or the perception that the input control devices 36 are integral with the tools 14 so that the operator S has a sense of directly controlling the tools 14. In other embodiments, the input control devices 36 may have more or fewer degrees of freedom than the associated medical tools and still provide the operator S with telepresence. To this end, position, force, and tactile feedback sensors may be employed to transmit position, force, and tactile sensations from the tools 14 back to the operator S's hands through the input control devices 36. An operator input system 16 of the operator's console 38 may also include input control devices 37, which are foot pedals that receive input from an operator's foot.

Figure 2:
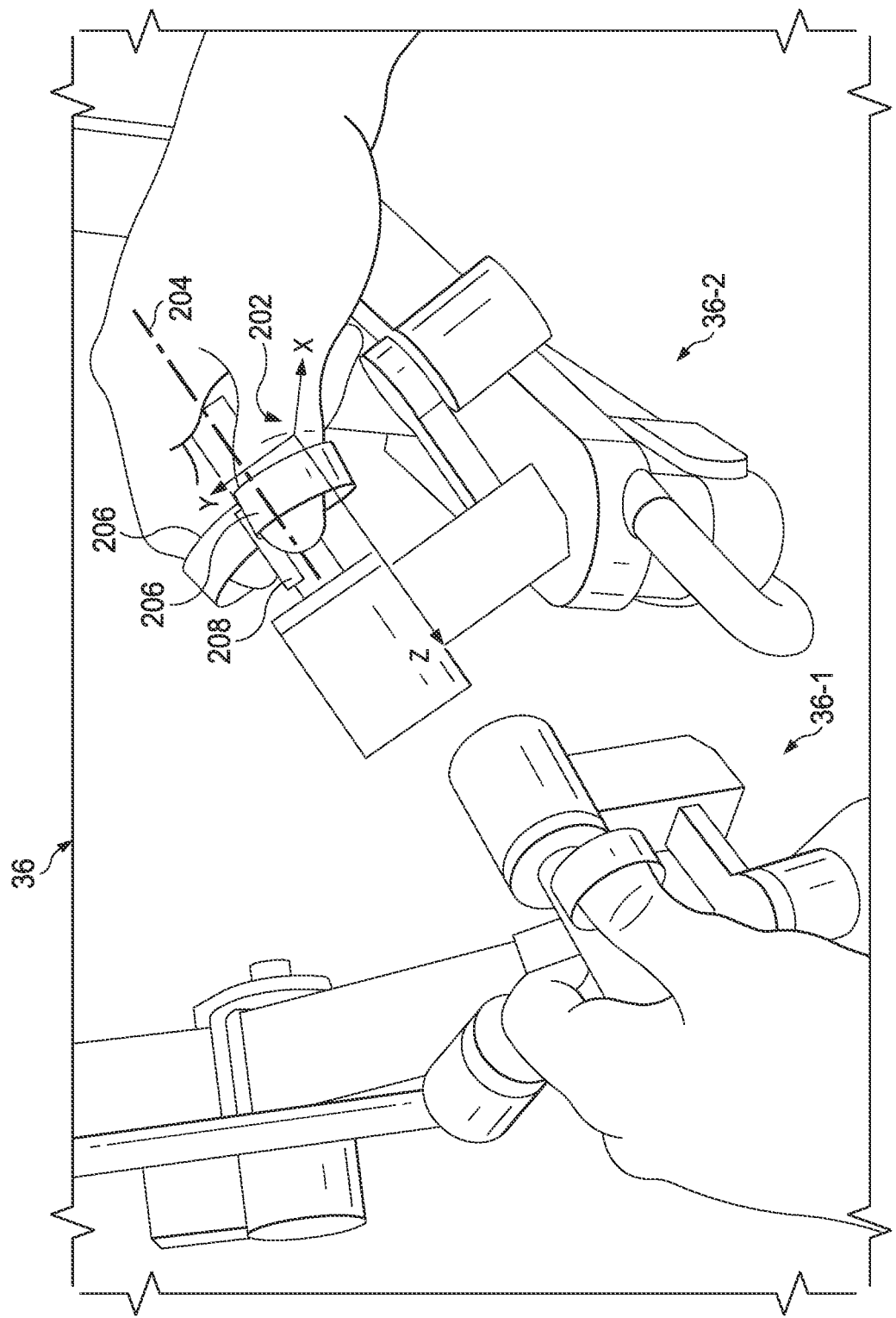
FIG. 2 is a perspective view of an operator's input controller, in accordance with an embodiment of the present disclosure.

As show in FIG. 2, in some embodiments, input control devices 36 may include a left-hand input control device 36-1 (e.g., receiving input from an operator's left hand) and a right-hand input control device 36-2 (e.g., receiving input from an operator's right hand). The left-hand input control device 36-1 and right-hand input control device 36-2 may be used by an operator to control their associated medical tools 14 and/or 15 using the corresponding manipulator respectively. Each of the input control devices 36-1 and 36-2 may include one or more of any number of a variety of input devices such as grip inputs 206 and trigger switches 208. A master reference frame associated with each of the input control devices 36-1 and 36-2 may be provided. As illustrated in the example of FIG. 2, a master reference frame 202 associated with the input control device 36-2 is provided. The Z-axis of the master reference frame 202 is parallel to an axis of symmetry 204 of the input control device 36-2. The X and Y axes of the master reference frame 202 extend perpendicularly from the axis of symmetry 204. In some embodiments, alternatively or additionally, an operator may control medical tools 14 and/or 15 using body motion and gestures (e.g., hand motion, hand gesture, eye movement) using an image or motion tracking system.

Figure 3A:
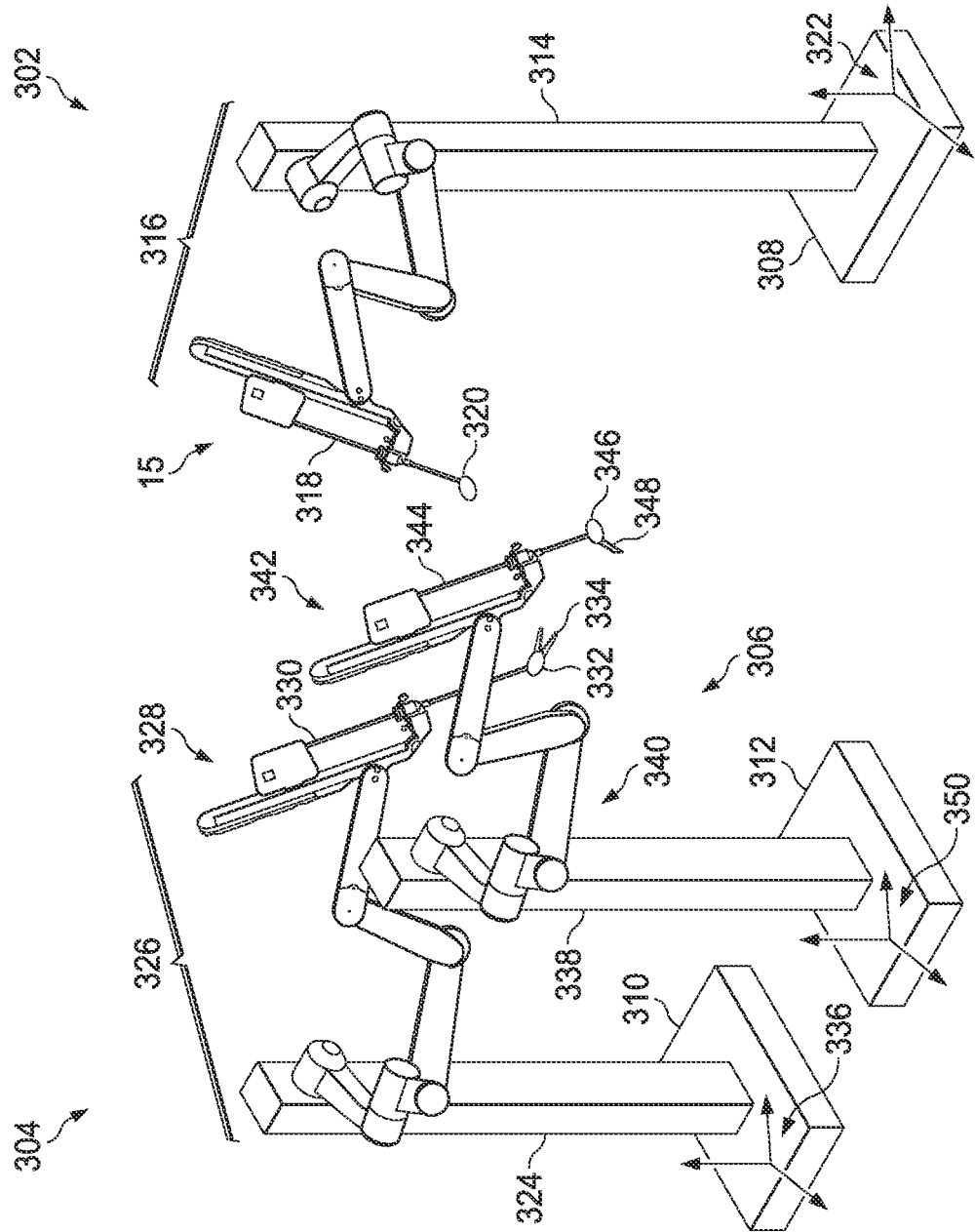
FIG. 3A is a perspective view of three manipulator assemblies of a robotic medical system, in accordance with an embodiment of the present disclosure.
Figure 3B:
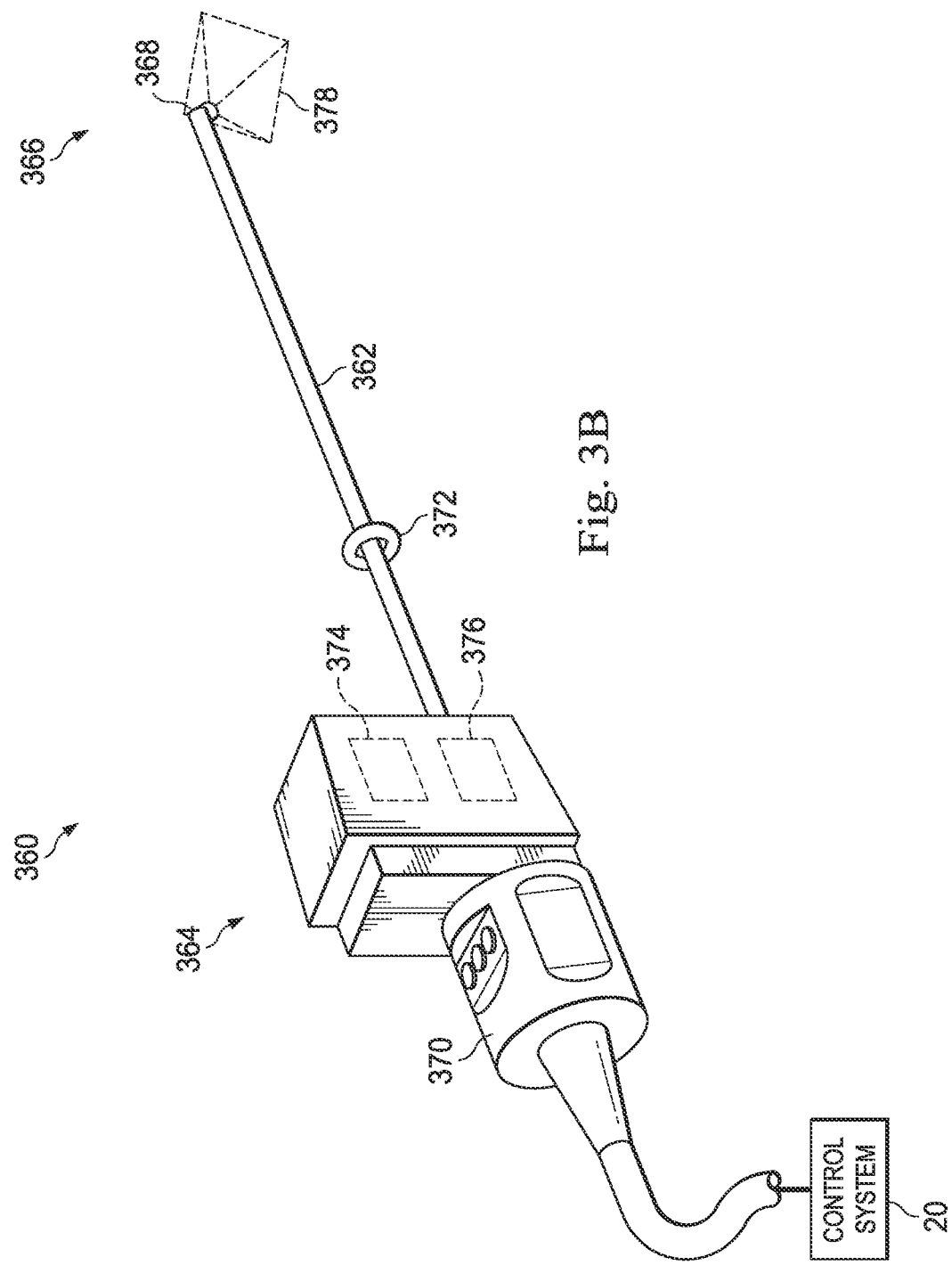
FIG. 3B is a perspective view of a tool of a robotic medical system, in accordance with an embodiment of the present disclosure.

Referring to FIGS. 3A and 3B, in various embodiments, a robotic system (e.g., a medical robotic system) may include a plurality of tools (e.g., medical tools 14 and/or 15) that may be controlled by robotic manipulators, human manipulators, and/or a combination thereof. In some embodiments, one or more tools may be designed to be mounted to a fixture. The fixture can be adjusted manually or with input devices located on or adjacent to it. In some embodiments, one or more tools may be operably coupled to a corresponding teleoperational manipulator of a teleoperational medical system (e.g., a teleoperational medical system where an operator controls the teleoperational manipulator using an operator's console). For example, as shown in FIG. 1B, the teleoperational manipulators of two or more tools may share the same base (e.g., a base 58). For further example, as shown in FIG. 3A, teleoperational manipulators of two or more tools may have separate bases. In some embodiments, as shown in FIG. 3B, one or more tools may be hand held and controlled by one or more human manipulators. For example, an operator may use his or her hands to move a proximal housing of the tool to control the tool.

Referring to the example of FIG. 3A, illustrated is a robotic system (e.g., a robotic medical system 10 of FIG. 1A) including three manipulator assemblies 302, 304, and 306 with separate bases 308, 310, and 312 respectively. The manipulator assembly 302 includes a base 308, a structure support 314, and a manipulator 316. In the example of FIG. 3, an imaging tool 15 is mounted on the manipulator 316, and thus the manipulator assembly 302 can be considered to further include the mounted imaging tool 15. The imaging tool 15 includes a shaft 318 and an imaging device 320. The imaging device 320 may include for example an optical imager, an ultrasonic imager, an electromagnetic imager such as a fluoroscopic imager, a thermal imager, a thermoacoustic imager, volumetric imaging devices such as computed tomography (CT) and magnetic resonance imaging (MRI) imagers, and any other suitable imagers.

As illustrated in FIG. 3A, the base 308 has a reference frame 322. The robotic system also includes a manipulator assembly 304. The manipulator assembly 304 includes a base 310 that is physically separate and independent from the base 308 of the manipulator assembly 302. The manipulator assembly 304 includes a structural support 324 and a manipulator 326. In the example of FIG. 3A, a tool 328 (e.g., medical tool 14) is mounted on the manipulator 326, and thus the manipulator assembly 304 can be considered to further include the mounted tool 328. The tool 328 includes a shaft 330, a wrist 332 coupled to the distal end of the shaft 330, and an end effector 334 coupled to the wrist 332. The base 310 has a reference frame 336.

In the example of FIG. 3A, the robotic system also includes a manipulator assembly 306. The manipulator assembly 306 includes a base 312 that is physically separate and independent from the base 308 of the manipulator assembly 302 and the base 310 of the manipulator assembly 304. The manipulator assembly 306 includes a structural support 338 and a manipulator 340. In the example of FIG. 3, a tool 342 (e.g., medical tool 14) is mounted on the manipulator 340, and thus the manipulator assembly 306 can be considered to further include the mounted tool 342. The tool 342 includes a shaft 344, a wrist 346 coupled to the distal end of the shaft 344, and an end effector 348 coupled to the wrist 346. The base 312 has a reference frame 350. While in the example of FIG. 3A, the bases 308, 310, and 312 are physically separate and independent from each other, in alternative embodiments, manipulators of a robotic system are not physically separate, and one or more uninstrumented links or joints (i.e., without sensors that provide sufficient information for determining all of the spatial translational and orientational parameters of the link or joint) may connect the manipulators. In some embodiments, the transformation between references frames for the bases are measured and known. In alternative embodiments, the transformation between reference frames for the bases are unknown.

Referring to FIG. 3B, illustrated is a medical tool 360. In some embodiments, the medical tool 360 is designed to be mounted to a fixture that can be adjusted manually or with input devices located on or adjacent to the fixture. In some embodiments, the medical tool 360 is operably coupled to a teleoperational manipulator of a teleoperational medical system. As illustrated in FIG. 3B, the medical tool 360 includes an elongate shaft 362 having a proximal end 364 and a distal end 366. A distal portion 368 (e.g., an end effector, an imaging device, etc.) is disposed at the distal end 366 of the shaft 362. In an example, the distal portion 368 is articulatable. A proximal housing 370 is disposed at the proximal end 364 of the shaft 362. The medical tool 360 may include an actuation assembly 374 for driving motion of the articulatable distal portion 368. In some embodiments, the actuation assembly 374 may be detached from the proximal portion of the medical tool 360. A sensor system 376 may be used for sensing the motion of the shaft 362. In some embodiments, the sensor system 376 is included in the medical tool 360. For example, the sensor system 376 and actuation assembly 374 may be disposed in the proximal housing 370. For a further example, as illustrated in FIG. 3B, the sensor system 376 and actuation assembly 374 may be disposed on the shaft 362 next to the proximal housing 370. Alternatively, in some embodiments, the sensor system 376 is not included in the medical tool 360. In various embodiments, the sensor system 376, the actuation assembly 374, and the proximal housing 370 are in communication with a control system (e.g., the control system 20 of FIG. 1).

In some embodiments, the medical tool 360 is a hand-held device, and an operator may use his or her hands to move the proximal housing 370 to control the movement of the shaft 362 in one or more degrees of freedom relative to the proximal housing 370.

In some embodiments, the medical tool 360 is operably coupled to a teleoperational manipulator of a teleoperational medical system. The proximal housing 370 may be removably connectable to the teleoperational medical system for releasably mounting and interfacing the medical tool 360 to a teleoperational manipulator of the teleoperational medical system. The proximal housing 370 may transmit drive signals and/or motion input from the teleoperational medical system to move the shaft 362 in at least one degree of freedom relative to the proximal housing 370.

In the illustrated example of FIG. 3B, the shaft 362 passes through a fulcrum pivot point 372 (indicated by a ring in FIG. 3B) of the medical tool 360, and the articulatable distal portion 368 includes an imaging device. The imaging device has a field of view 378. In the illustrated example of FIG. 3B, the field of view 378 has a three-dimensional pyramidal frustum shape. In some embodiments, the imaging device is a stereoscopic imaging instrument with two imaging devices, and the field of view 378 of the imaging device is the combined volume of the three-dimensional pyramidal frustums for each imaging device of the imaging device. In alternative embodiments, the field of view for the imaging device may provide another region of visualization, such as by providing a conical frustum shape, a slice-of-pie shape, or some other shape. The imaging device may capture images of tools and natural features within the patient anatomy. In some embodiments, the imaging device (e.g., a magnetic resonance imaging (MRI) device, a computed tomography (CT) scan device, etc.) may be located outside of the patient, and in those embodiments, a visual feedback of the tool motion be derived from a series of three-dimensional (3D) images.

Figure 4A:
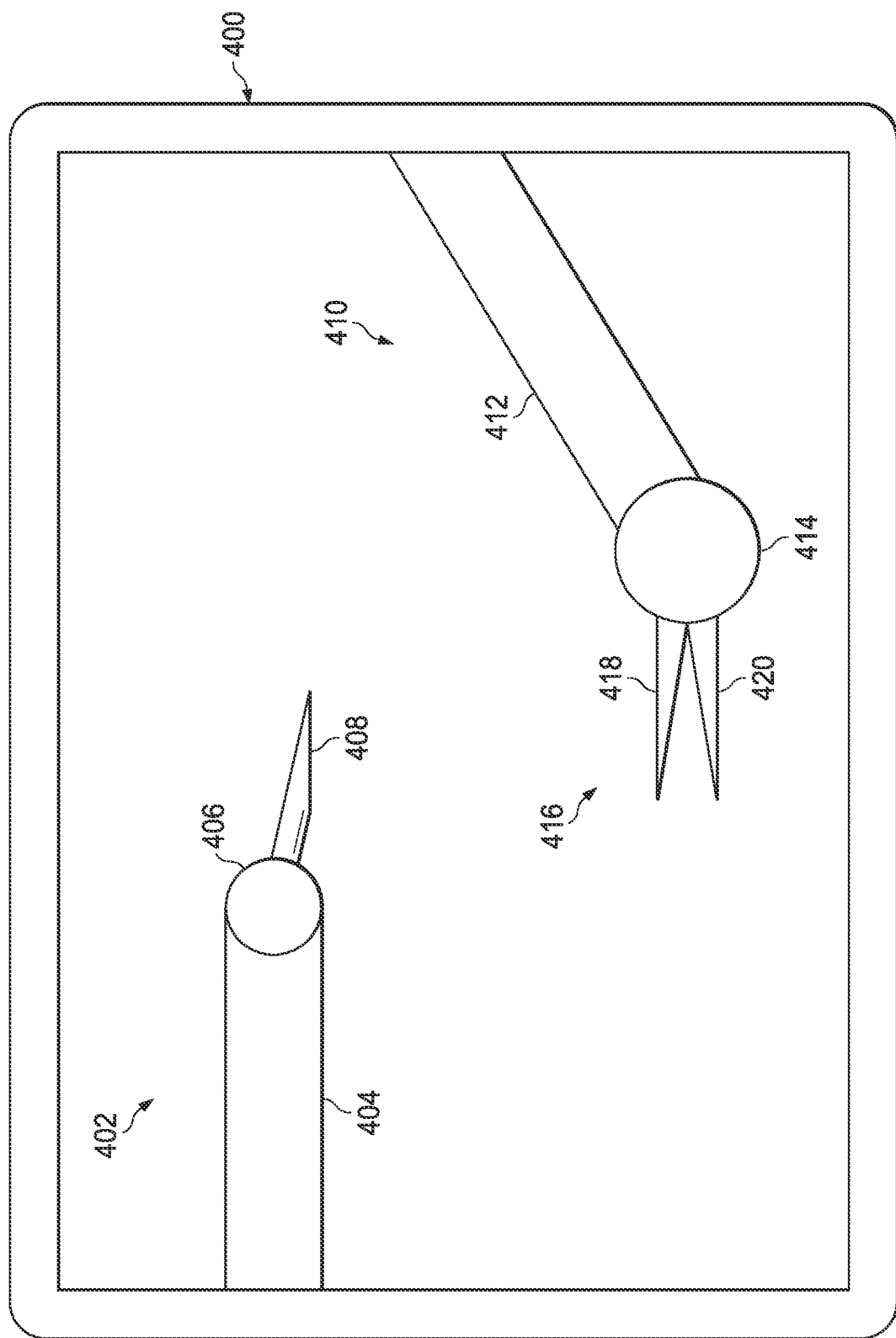
FIG. 4A is an imaging view through a display of an operator's control console in accordance with an embodiment of the present disclosure.

Referring to FIGS. 4A and 4B, image data from an imaging device may be provided to an operator using a display. Referring to FIG. 4A, illustrated therein is a display 400 (e.g., a display of operator's console 38) providing an image from the imaging device 320, which shows portions of the tools 328 and 342 that are in the field of view of the imaging device 320 (e.g., the imaging device 320 of the manipulator assembly 302 of FIG. 3). In the example of FIG. 4A, the tools 328 and 342 have end effectors of different shapes respectively, and as such, their corresponding images (also referred to as image-space tools) also have end effectors of different shapes respectively. As illustrated in FIG. 4A, the display 400 includes an image-space tool 402 corresponding to one of the tools 328 and 342. The image-space tool 402 includes a portion of a shaft 404, a wrist 406, and an end effector 408, where the end effector 408 may be a needle, a scalpel, a monopolar cautery hook, or any other suitable end effector. The display 400 further includes an image-space tool 410 corresponding to the other of the tools 328 and 342. The image-space tool 410 includes a portion of a shaft 412, a wrist 414, and an end effector 416. The end effector 416 includes two jaws 418 and 420.

Referring to FIG. 4B, in some embodiments, the multiple tools (e.g., tools 328 and 342) may have the same or substantially similar appearances. As such, their corresponding image-space tools in the captured image also have end effectors with substantially similar appearances. In the example of FIG. 4B, a display 400 (e.g., a display of operator's console 38) including a captured image from the imaging device 320, which shows portions of the tools 328 and 342 that are in the field of view of the imaging device 320 (e.g., the imaging device 320 of the manipulator assembly 302 of FIG. 3A). Specifically, the display 400 includes an image-space tool 450 corresponding to one of the tools 328 and 342. The image-space tool 450 includes a portion of a shaft 452, a wrist 454, and an end effector 456, where the end effector 456 includes two jaws 457 and 458. The display 400 further includes an image-space tool 460 corresponding to the other of the tools 328 and 342. The image-space tool 460 includes a portion of a shaft 462, a wrist 464, and an end effector 466. The end effector 466 includes two jaws 468 and 470. In the example of FIG. 4B, the tools 328 and 342 have end effectors with substantially similar appearances. As such, their corresponding image-space tools in the captured image also have end effectors with substantially similar appearances, which may cause an ambiguity problem in mapping between tools 328 and 342 to image-space tools 450 and 460. Such ambiguity in the mapping may cause issues (e.g., affecting intuitiveness, affecting accuracy of information displayed to an operation, etc.) in various applications (e.g., registration, applications for overlaying tool information on images of corresponding tools in a display) that depend on accurate mapping between tools 328 and 342 and image-space tools 450 and 460.

As discussed in detail below, a disambiguation process may be used to solve the ambiguity problem. While a registration application using the disambiguation process is used as an example herein, the disambiguation process may be used in any applications (e.g., applications for overlaying tool information on images of corresponding tools in a display, that depend on accurate mapping between tools and image-space tools.

In various embodiments, a registration process may be performed using the image data from the imaging device, which may be used to improve the intuitiveness of a teleoperational system. For example, the registration process may determine spatial alignments between the master control devices and their associated tools/end effectors (also referred to as a master-tool alignment) and master-tool transformations. Such spatial alignments may be used to provide effective control relationships between the master control devices and their respective slave tools/end effectors. Each spatial alignment between a master control device and its slave tool may provide a reasonably accurate relationship between the operator's perceived motion of the master control device (e.g., a proprioceptive sense) and the operator's perceived resulting motion of the tool including the shaft and the end effector (e.g., a visual sense). For example, if the operator moves a hand grasping a master control device to the left, the operator expects to perceive the associated slave tool/end effector to move to the left also. If the perceived spatial motions match, then the operator can easily control the slave's movement by moving the master control device. But if the perceived spatial motions do not match (e.g., a master control device movement to the left results in a slave movement up and to the right), then it is difficult for the operator to control the slave's movement by moving the master control device.

However, during the image-based registration process, ambiguity in establishing the correspondence between the multiple image-space tools (e.g., image-space tools 402 and 410 of FIG. 4A, image-space tools 450 and 460 of FIG. 4B) in the image data and the respective physical tools and their associated manipulators may arise, which may affect the intuitiveness of a teleoperational system. In various embodiments, such ambiguity may arise where the master-tool transformations are unknown in part or whole (e.g., because of unknown transformations between a camera reference frame of the imaging device and a tool reference frame of a tool). In some examples, the tools (e.g., imaging tool 15 and tools 328 and 342) are controlled by manipulators that have separate bases and do not share a common mechanical reference. In some examples, the tools (e.g., imaging tool 15 and tools 328 and 342) are controlled by manipulators that have the same base but not all degrees of freedom between those manipulators are measured (e.g., by sensors in the manipulators). In some examples, the tools are so physically close to each other, such that manipulator data (e.g., sensor data including joint encoders data from the manipulators, kinematics information of the manipulators) is not sufficient to disambiguate the correspondences between image-space tools and physical tools. In some examples, one or more of the tools (e.g., imaging tool 15 and tools 328 and 342) are hand-held tools operated by human manipulators.

Referring to FIGS. 5 through 11, various systems and methods for performing a disambiguation process are described. As described in detail below, a disambiguation process may be used to generate the correct correspondences between image-space tools in the image data and their respective tools, which may then be used to determine the master-tool alignment and a master-tool transformation during a registration process. Different disambiguation processes may be performed based on the disambiguation settings (e.g., motion-based, pose-based, appearance-based, operator-specified) associated with the corresponding tools. In various embodiments, the disambiguation settings may include various types and values of disambiguation parameters for performing the disambiguation processes, and may be configured by an operator.

Figure 5:
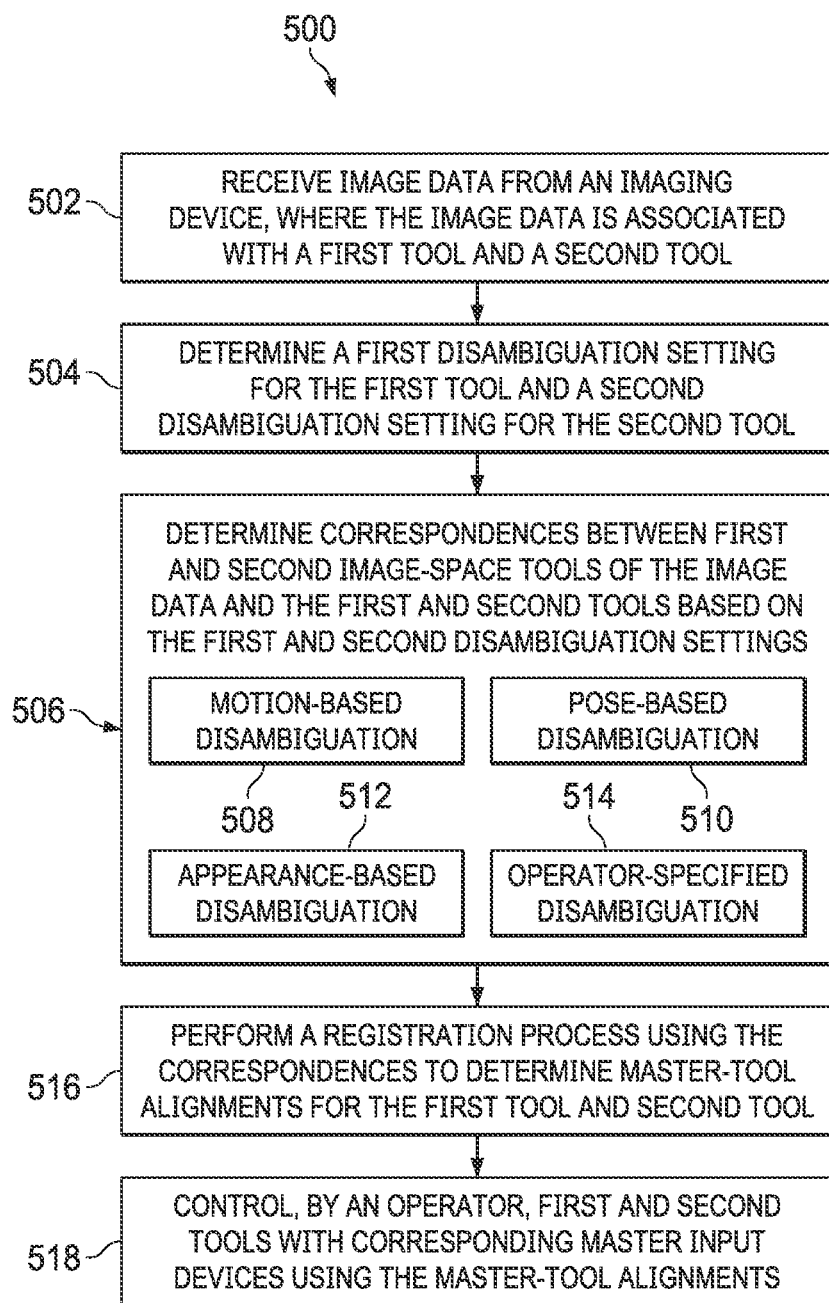
FIG. 5 illustrates a flowchart providing a method for performing a disambiguation process or a portion thereof for master-tool registration, in accordance with an embodiment of the present disclosure.

Referring to FIG. 5, illustrated therein is a method 500 for performing a disambiguation process. The method 500 is illustrated in FIG. 5 as a set of operations or processes 502 through 518. Not all of the illustrated processes 502 through 518 may be performed in all embodiments of method 500. Additionally, one or more processes that are not expressly illustrated in FIG. 5 may be included before, after, in between, or as part of the processes 502 through 518. In some embodiments, one or more of the processes may be implemented, at least in part, in the form of executable code stored on non-transitory, tangible, machine-readable media that, when run by one or more processors (e.g., the processors of a control system such as control system 20), causes the one or more processors to perform one or more of the processes.

In various embodiments, the method 500 may be performed before or during an operation (e.g., a medical operation). In a medical example, the method 500 may be performed before the medical operation (e.g. during set-up) outside of the patient or inside the patient. In an example, the method 500 may be performed after the plurality of image-space tools are captured in the image data but prior to connecting control loops between the plurality of tools and their respective master input devices. In another example, the method 500 may be performed during the medical operation.

The method 500 begins at process 502, where a control system (e.g., control system 20 of FIG. 1) receives image data from an imaging device of a robotic medical system. The robotic medical system may include multiple tools controlled by respective manipulators. In the example of FIG. 3A, the robotic medical system includes tools 15, 328, and 342 controlled by manipulators 316, 326, and 340 respectively. At process 502, a display 400 displays an image captured by the imaging device 320 of the imaging tool 15. As shown in the example of FIGS. 4A and 4B, the captured image includes image-space tools corresponding to tools 328 and 342. In an example, the captured image is provided to an operator through a display of an operator's console (e.g., operator's console 38).

The method 500 may then proceed to process 504, where a control system (e.g., control system 20) determines first and second disambiguation settings for first and second tools (e.g., tools 328 and 342) respectively. Each of the first and second disambiguation settings may have a type selected from various disambiguation setting types including, for example, motion-based disambiguation setting, pose-based disambiguation setting, appearance-based disambiguation setting, operator-specified disambiguation setting, any suitable type of disambiguation settings, or a combination thereof. In some embodiments, the disambiguation settings for the tools may be determined based on the properties of the tools (e.g., tools having substantially the same appearance) and operation performance requirements (e.g., workflow continuity, susceptibility to operator error). In an example, as shown in FIG. 4A where tools 328 and 342 have different end effector appearances, the control system may determine that appearance-based disambiguation settings may be used for both tools. In another example, as shown in FIG. 4B where tools 328 and 342 have substantially the same appearance, appearance-based disambiguation settings may not be effective for disambiguation. In that example, the control system may determine that motion-based disambiguation settings and/or pose-based disambiguation settings may be used for the tools.

In various embodiments, two tools may have disambiguation settings of the same type or of different types. In some embodiments, two tools have disambiguation settings having the same type but different disambiguation parameter values (e.g., different disambiguation periods for moving the corresponding tools, different motion types, different motion amounts, etc.). For example, the first and second disambiguation settings have the same type (e.g., a motion-based disambiguation setting) may have different motion types (e.g., rotation and translation respectively). In another example, the first and second disambiguation settings have the same motion type (e.g., a vibration motion, a rotation motion) but with different motion parameters (e.g., different vibration frequencies, different rotation amounts).

In some embodiments, the first and second disambiguation settings are of different disambiguation setting types. For example, the first disambiguation setting is one of the group including a motion-based disambiguation setting, a pose-based disambiguation setting, an appearance-based disambiguation setting, and an operator-specified disambiguation setting. The second disambiguation setting is another of the group including the motion-based disambiguation setting, the pose-based disambiguation setting, the appearance-based disambiguation setting, and the operator-specified disambiguation setting.

The method 500 may proceed to process 506, where the control system determines the correspondences between first and second image-space tools of the image data and the first and second tools based on the first and second disambiguation settings. At process 506, based on the first and second disambiguation settings, corresponding disambiguation processes (e.g., one of disambiguation processes 508, 510, 512, and 514) may be performed. Those different disambiguation processes will be described in detail with reference to FIGS. 6 through 11.

The method 500 may proceed to process 516, where the control system performs a registration process using the correspondences between first and second image-space tools of the image data and the first and second tools, and determines master-tool alignments for the first tool and second tool. For example, master-tool transformations for each of the first and second tools may be determined based on the first and second image-space tools and the correspondences. In some embodiments, the registration process uses at least some of the same data utilized for disambiguation (e.g., at process 506). As a specific example, in one embodiment, the process 506 uses an appearance-based disambiguation setting comprising geometric information about the tool, and the process 516 uses at least some of the same geometric information for registration. As another specific example, in one embodiment, the process 506 uses a pose-based disambiguation setting comprising pose information for one or more portions of the tool, and the process 516 uses at least some of the same pose information for registration.

The method 500 may proceed to process 518, where an operator controls the first and second tools using corresponding master input devices using the master-tool alignments determined during the registration process. Such master-tool alignments may be used to improve the intuitiveness of the robotic medical system.

Figure 6:
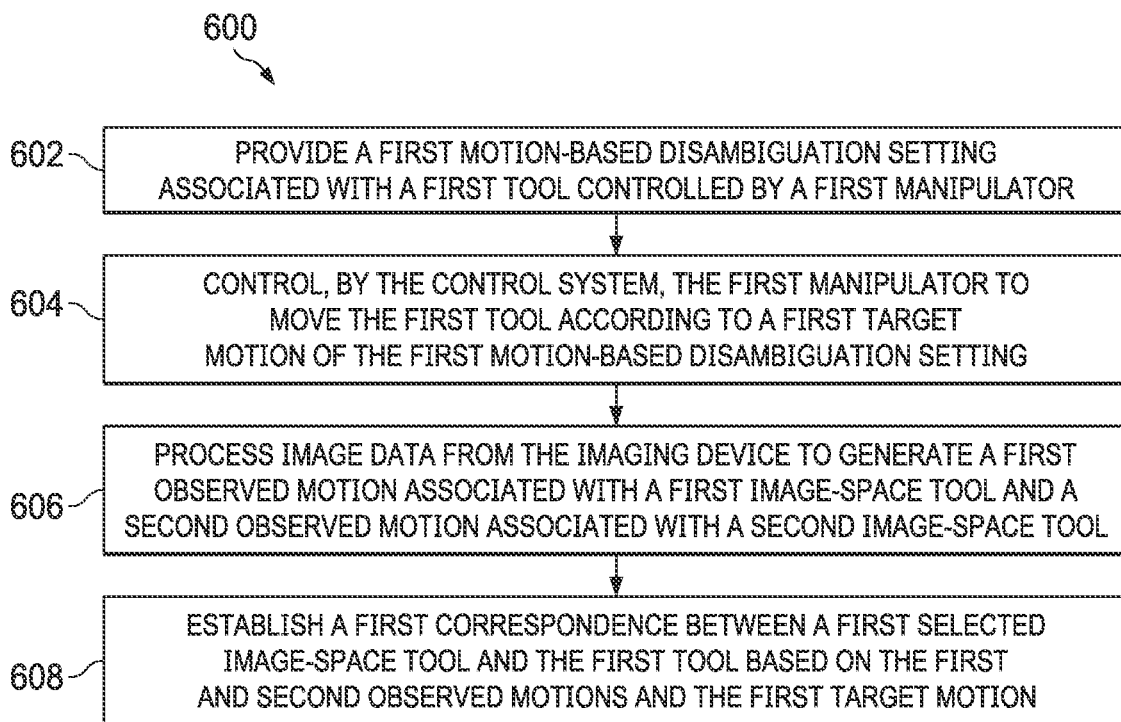
FIG. 6 illustrates a flowchart providing a method for performing a disambiguation process or a portion thereof for master-tool registration using a control system commanded motion, in accordance with an embodiment of the present disclosure.
Figure 7:
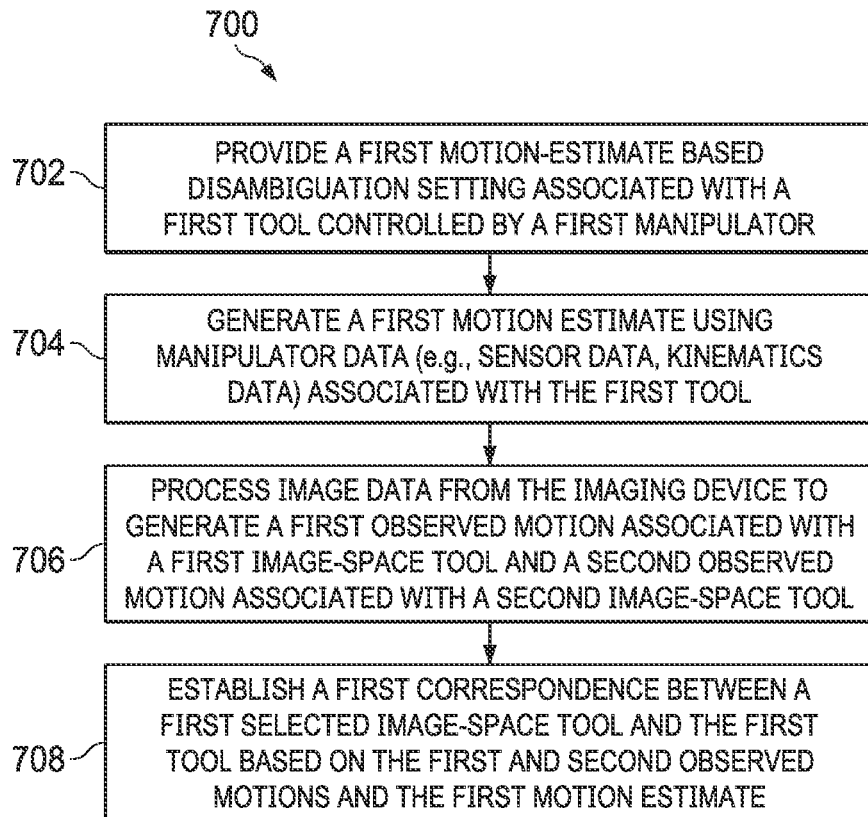
FIG. 7 illustrates a flowchart providing a method for performing a disambiguation process or a portion thereof for master-tool registration using a motion estimate, in accordance with an embodiment of the present disclosure.
Figure 8:
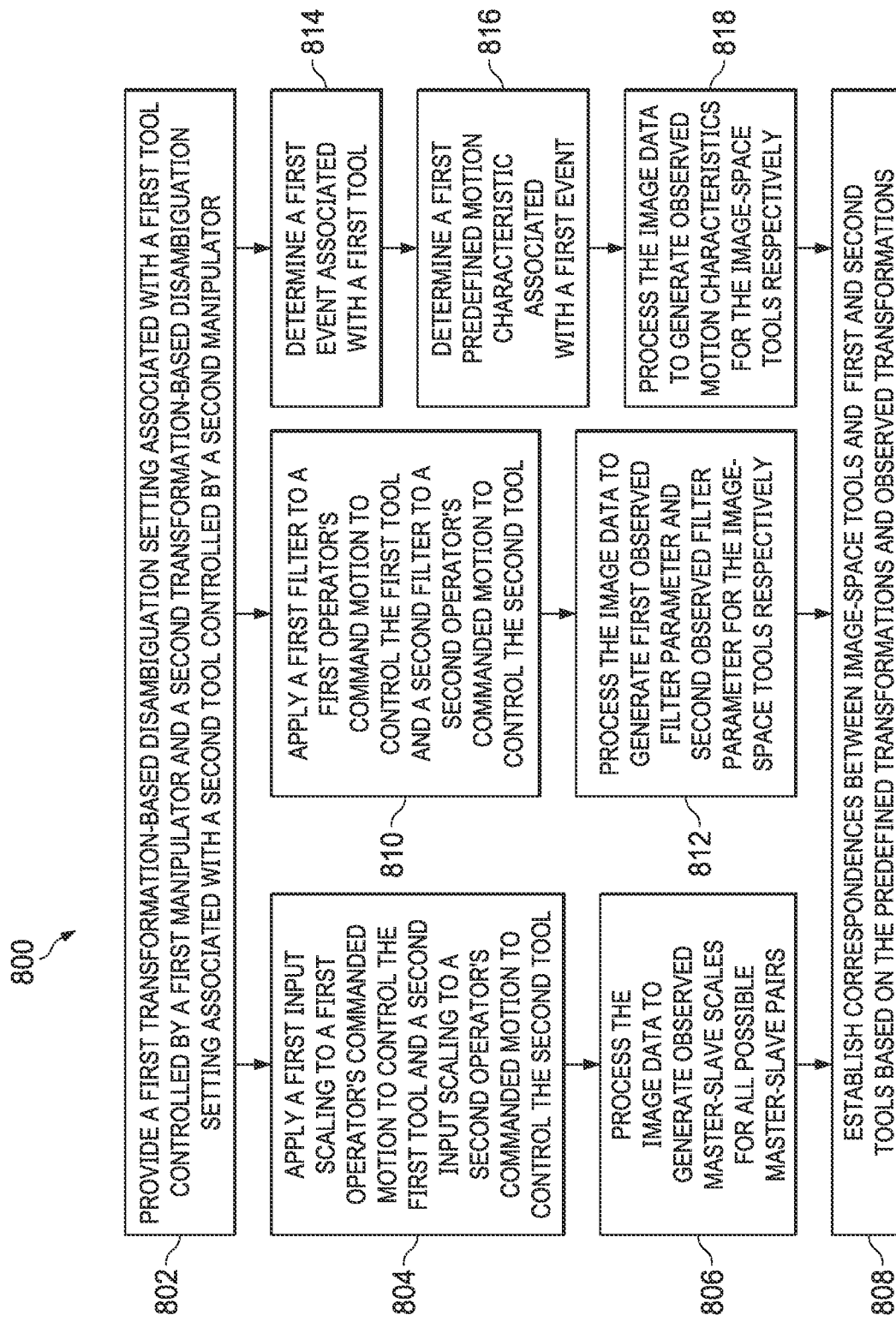
FIG. 8 illustrates a flowchart providing a method for performing a disambiguation process or a portion thereof for master-tool registration using a transformation of an operator commanded motion, in accordance with an embodiment of the present disclosure.
Figure 9:
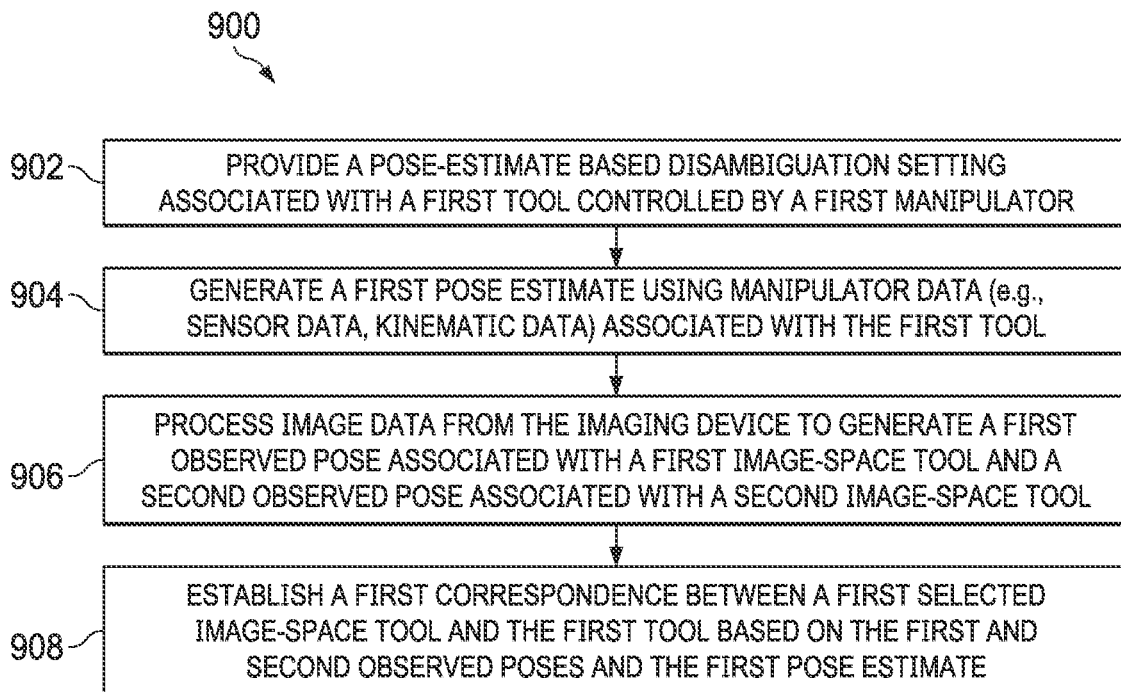
FIG. 9 illustrates a flowchart providing a method for performing a disambiguation process or a portion thereof for master-tool registration using a pose estimate, in accordance with an embodiment of the present disclosure.
Figure 10:
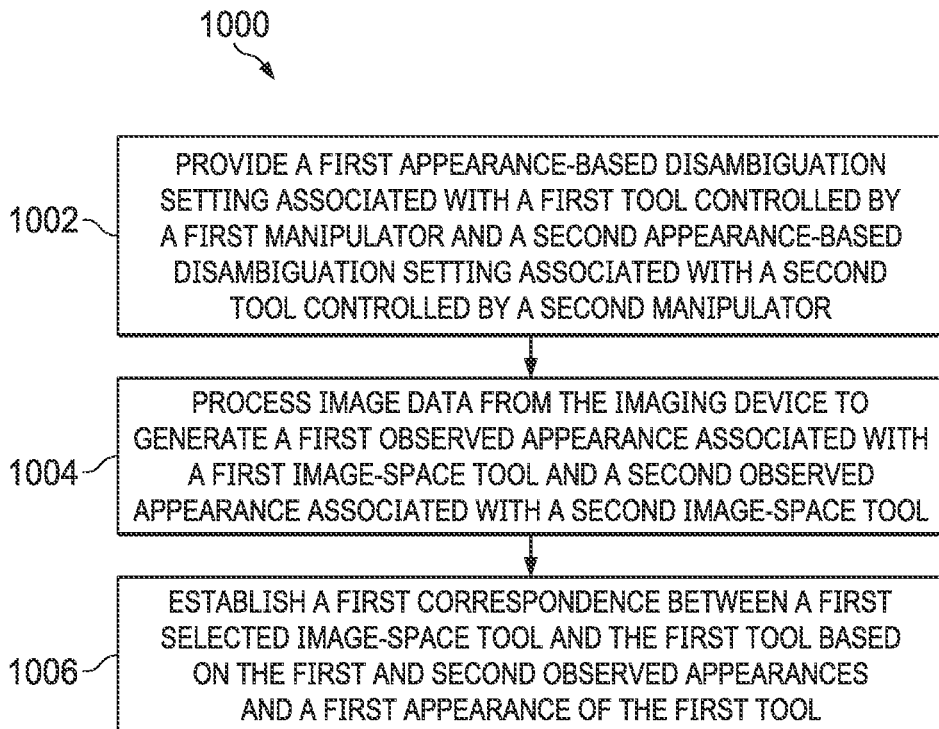
FIG. 10 illustrates a flowchart providing a method for performing a disambiguation process or a portion thereof for master-tool registration using an appearance-based disambiguation setting, in accordance with an embodiment of the present disclosure.
Figure 11:
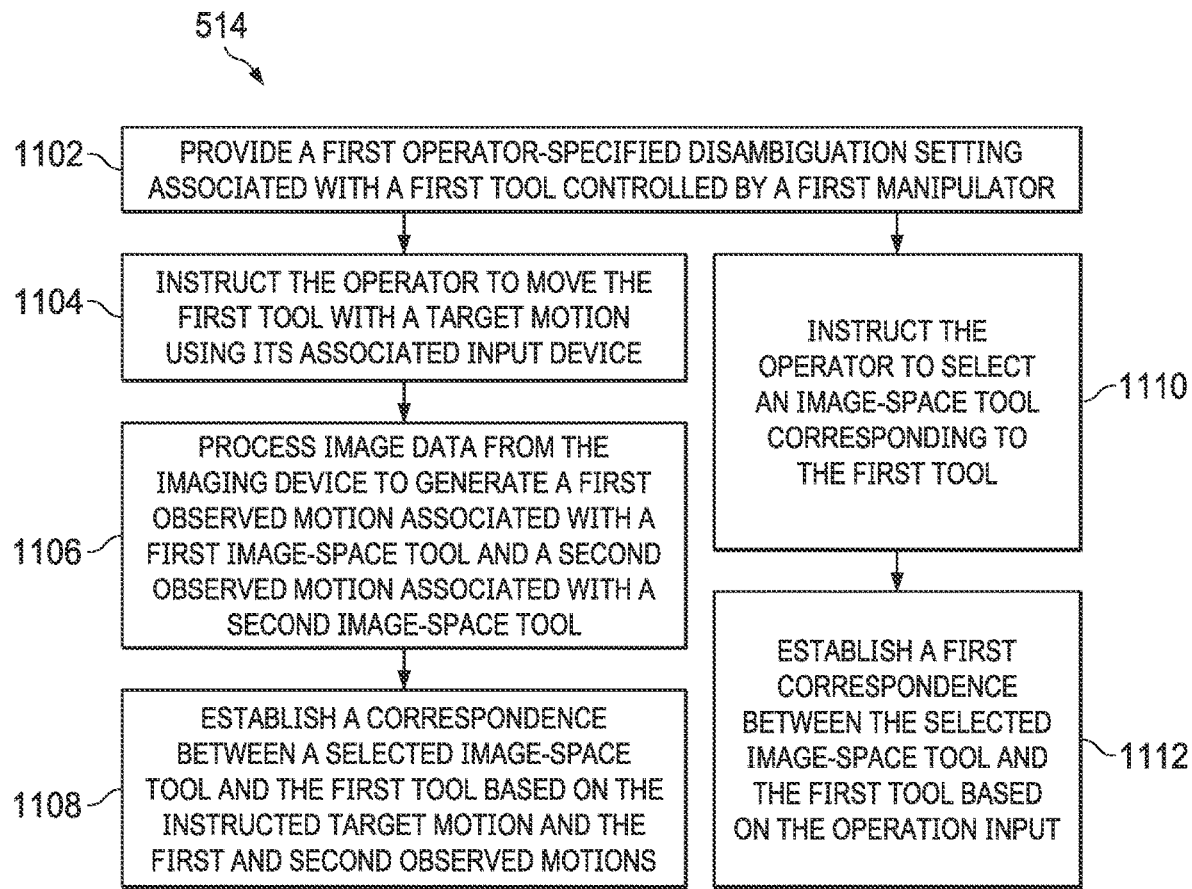
FIG. 11 illustrates a flowchart providing a method for performing a disambiguation process or a portion thereof for master-tool registration using an operator-specified disambiguation setting, in accordance with an embodiment of the present disclosure.

Referring to FIGS. 6 through 11, various disambiguation processes may be performed (e.g., at process 506 of FIG. 5) to determine the correspondences between first and second image-space tools of the image data and the first and second tools. FIGS. 6, 7, and 8 illustrate different disambiguation processes using different motion-based disambiguation settings respectively. FIG. 9 illustrates a disambiguation processes using pose-based disambiguation settings. FIG. 10 illustrates a disambiguation processes using appearance-based disambiguation settings. FIG. 11 illustrates a disambiguation processes using operator-specified disambiguation settings.

Referring to FIG. 6, illustrated is a motion-based disambiguation method 600 (e.g., motion-based disambiguation process 508 of FIG. 5), where a control system controls a particular robotic manipulator to move its corresponding tool based on a target motion provided by a motion-based disambiguation setting for that tool. In various embodiments, such a target motion for that tool is unique among motions of other tools visible in the image data, which may be used to identify a corresponding image-space tool for that tool. In some embodiments, the target motion is determined based on imaging device types and/or motion estimation accuracy for different motion types. In an example, a jaw open/close motion may be chosen over a shaft roll motion because the shaft roll motion is more difficult to estimate. In another example where the imaging device is monoscopic and has no depth information, a two-dimensional (2D) target motion in the monoscopic imaging device's 2D imaging space is chosen. In some embodiments, the target motion(s) may be determined by selecting a motion trajectory and motion estimation approach that is invariant to alignment of the camera relative to the motion (e.g., where the transformation between camera space and manipulator space is known). In an example, the target motions include a series of motions in orthogonal planes.

The method 600 is illustrated in FIG. 6 as a set of operations or processes 602 through 608. Not all of the illustrated processes 602 through 608 may be performed in all embodiments of method 600. Additionally, one or more processes that are not expressly illustrated in FIG. 6 may be included before, after, in between, or as part of the processes 602 through 608. In some embodiments, one or more of the processes may be implemented, at least in part, in the form of executable code stored on non-transitory, tangible, machine-readable media that, when run by one or more processors (e.g., the processors of a control system such as control system 20), causes the one or more processors to perform one or more of the processes.

The method 600 begins at process 602, where the control system determines that a first motion-based disambiguation setting is associated with a first tool controlled by a first robotic manipulator. The motion-based disambiguation setting may include a target motion for the first tool. The target motion may include a rotational motion (e.g., roll, yaw, pitch) of the tool or a portion thereof (e.g., an end effector), a translational motion (e.g., insertion, withdrawal, lateral movement), or a vibration motion (e.g., along a particular axis) at a particular frequency. In some embodiments, the target motion is a roll motion where a tip of the end effector does not move. In some embodiments, the target motion includes a withdrawal motion of a first amount followed by an insertion motion of a second amount that is less than or equal to the first amount, such that after the target motion is performed, a tip of the end effector does not extend beyond its position prior to the target motion.

In some embodiments, at process 602, the control system determines that a second motion-based disambiguation setting is associated with a second tool controlled by a first robotic manipulator. In some examples, target motions of the first and second motion-based disambiguation settings are the same but to be performed at different times. In some examples, target motions of the first and second motion-based disambiguation settings are different. For example, target motions of the first and second motion-based disambiguation settings may have different motion types. For further example, target motions of the first and second motion-based disambiguation settings may have the same motion type (e.g., vibration motion) but different motion amounts or other motion parameters (e.g., motion amplitude or motion frequencies).

The method 600 may proceed to process 604, where the control system controls the first robotic manipulator to move the first tool according to the first target motion. In some embodiments, process 604 is performed during a disambiguation period in a medical procedure. For example, the disambiguation period may be determined using non-critical periods of a medical procedure, including, for example, a period when a tool is being introduced into a patient's body and before the tool is controlled by an operator. The disambiguation period may be during a portion of tool exchange or during clutching.

In some embodiments, the target motions may be performed by overlaying on top of an operator-commanded motion at certain times and/or during certain events or system states. In some embodiments, the target motion may have a motion amount that is difficult or impossible for the human operator to discern, and is invisible to a naked human eye. In some embodiments, the operator-commanded motion may be associated with an operator goal different from determining the correspondence between the image-space tool and the tool.

In some embodiments, the multiple tools may be moved in a specific sequence during a disambiguation period. For example, the sequence may include, in order, a first target motion of a first tool (e.g., vibration along its roll axis for 0.5 seconds), a second target motion of a second tool (e.g., vibration along its pitch axis for 0.7 seconds), etc.

The method 600 may proceed to process 606, where a control system may process the image data (e.g., feature extraction, object tracing) to determine first and second image-spaced tools and their respective observed motions. The image data may include a video including a sequence of frames, where each frame may include images of the plurality of tools. Various image processing algorithms may be used to determine an observed motion for each tool in the captured image. In some embodiments, image (e.g., still image, video) processing algorithms (e.g., a Eulerian Video Magnification algorithm) may be used to generate the observed motions for the respective tools in the images by magnifying motions that may be invisible to naked human eyes. In some examples, the motion disambiguation setting may provide distinct motion properties (e.g., frequency, amplitude, axis of motion) that may be used to generate the magnified motions. In some embodiments, there may be loss of motion information in motion estimation, and it is difficult to determine a correspondence between target motion and observed image motion. In those embodiments, additional motion-based disambiguation processes using a different target motion may be performed. Alternatively, disambiguation processes based on different types of disambiguation settings (e.g., pose-based disambiguation, appearance-based disambiguation, operator-specified disambiguation) may be performed.

The method 600 may proceed to process 608, where the control system establishes a first correspondence between a first selected image-space tool and the first tool based on the first and second observed motions and the first target motion. The first selected image-space tool may be selected from the first and second image-space tools. In an example, the first selected image-space tool is chosen because it has an observed motion (e.g., vibration along a roll axis for 0.5 seconds) that matches the first target motion, where the other unselected image-space tool has an observed motion (e.g., vibration along a pitch axis for 0.7 seconds) that does not match the first target motion. As such, in that example, the control system may establish a first correspondence between the first selected image-space tool and the first tool because the first selected image-space tool has an observed motion that matches the first target motion.

In some embodiments, at process 608, the control system establishes a second correspondence between a second selected image-space tool and the second tool based on the first and second observed motions and the second target motion. In an example, the second selected image-space tool is chosen because it has an observed motion (e.g., vibration along a pitch axis for 0.7 seconds) that matches the target motion of the motion-based disambiguation setting of the second tool. As such, in that example, the control system may establish a second correspondence between the second selected image-space tool and the second tool because the second selected image-space tool has an observed motion that matches the second target motion. Those correspondences may then be used in a registration to determine master-tool alignments for the first and second tools respectively, as discussed above with reference to process 516 of FIG. 5.

Referring to FIG. 7, illustrated is a motion-estimate-based disambiguation method 700 (e.g., motion-based disambiguation process 508 of FIG. 5) where a control system generates a motion estimate of a tool based on information of the associated manipulator/input device, including, for example, sensor information provided by a sensor system, kinematics information of the associated manipulator/input device, or a combination thereof. The control system may establish the correspondence between the tool and an image-space tool based on the motion estimate and an observed motion of the image-space tool using the image data. The method 700 is illustrated in FIG. 7 as a set of operations or processes 702 through 708. Not all of the illustrated processes 702 through 708 may be performed in all embodiments of method 700. Additionally, one or more processes that are not expressly illustrated in FIG. 7 may be included before, after, in between, or as part of the processes 702 through 708. In some embodiments, one or more of the processes may be implemented, at least in part, in the form of executable code stored on non-transitory, tangible, machine-readable media that, when run by one or more processors (e.g., the processors of a control system such as control system 20), causes the one or more processors to perform one or more of the processes.

The method 700 begins at process 702, where a control system provides a first motion-estimate-based disambiguation setting associated with a first tool controlled by a first manipulator and/or a first master input device. The first motion-estimate-based disambiguation setting may include various disambiguation parameters, including, for example, manipulator/input device data source types, motion estimate types, etc. The manipulator/input device data source types may include, for example, sensor data, kinematics data, or a combination thereof for motion estimate. In another example, the first motion-estimate-based disambiguation setting may provide motion estimate types including, for example, a velocity estimate type, an acceleration estimate type, a motion pattern type, etc.

The method 700 may proceed to process 704, where the control system generates a first motion estimate for the first tool using information associated with the first manipulator that is coupled to the first tool. Such a first motion estimate may be generated based on the first motion-estimate-based disambiguation setting. For example, the manipulator information may include data having the manipulator data source types (e.g., sensor information provided by a sensor system, kinematics information from the associated first robotic manipulator, or a combination thereof). The sensor system may include one or more sensors including, for example, an inertial measurement unit (IMU), an electromagnetic sensor, an optical tracking system, an image tracking system, a hybrid sensor system, encoders of the first manipulator, other suitable sensor systems, and a combination thereof. In an example, the image tracking system may include a camera external to the patient's anatomy and provide manipulator information (e.g., alignment information between the first manipulator and other manipulators and/or the patient, first manipulator movement information, etc.) using image tracking algorithms.

For further example, the first motion estimate may be generated according to the motion estimate types provided by the first motion-estimate-based disambiguation setting. The first motion estimate may include, for example, a velocity estimate, an acceleration estimate, a motion pattern, and/or any other suitable motion estimate types of the first tool or a portion thereof (e.g., a shaft, an end effector). In an example, a first motion estimate may include a first motion pattern indicating that the first tool moves in and out of the field of view of the imaging device 320 of the imaging tool 15 for a first period (e.g., about 10 seconds).

In some embodiments, at process 704, the control system may generate a second motion estimate for a second tool using manipulator/input device information (e.g., sensor data, kinematics data, historical tool state (e.g., motion, pose) data, or a combination thereof) associated with a second manipulator/second input device that is coupled to the second tool. The second motion estimate may be generated based on a second motion-estimate-based disambiguation setting associated with the second tool. In an example, the second motion estimate may include a second motion pattern indicating that the second tool moves side to side (e.g., between left and right sides) in the field of view of the imaging device 320 of the imaging tool 15 for a second period (e.g., same as the first period or different from the first period).

The method 700 may proceed to process 706, where the control system applies image processing algorithms to the image data from the imaging device, and generates a first observed motion associated with a first image-space tool and a second observed motion associated with a second image-space tool. In some embodiments, the first and second observed motions are generated based on the first and second motion-estimate-based disambiguation settings, where each of the first and second observed motions may include observed motion data corresponding to the motion estimate types.

The method 700 may proceed to process 708, where the control system establishes a first correspondence between a first selected image-space tool and the first tool based on the first and second observed motions and the first motion estimate of the first tool. In some examples, the control system determines that an observed motion (e.g., an observed velocity, an observed acceleration, an observed motion pattern) of a first selected image-space tool from the first and second image-space tools match the first motion estimate (e.g., a velocity estimate, an acceleration estimate, a motion pattern), and establishes a correspondence between that first selected image-space tool and the first tool. In an example, the observed motion of the first selected image-space tool includes an observed motion pattern of moving in and out of the FOV of the imaging device, and the first motion estimate of the first tool also includes a motion pattern of moving in and out of the FOV of the imaging device.

In some embodiments, at process 708, the control system establishes a second correspondence between a second selected image-space tool and the second tool based on the first and second observed motions and the second motion estimate of the second tool. In an example, the second selected image-space tool is chosen because it has an observed motion (e.g., an observed motion pattern of moving from side to side) that matches the second motion estimate (e.g., a motion pattern of moving from side to side) of the second tool. Those first and second correspondences may then be used in a registration to determine master-tool alignments for the first and second tools respectively, as discussed above with reference to process 516 of FIG. 5.

Referring to FIG. 8, illustrated is a transformation-based disambiguation method 800 (also referred to as a modification-based disambiguation method 800) that may be used in process 508 of FIG. 5, where a control system may use a transformation (also referred to as a modification) associated with an operator's commanded motion for disambiguation. The transformation/modification may be provided in a transformation-based disambiguation setting (also referred to as a modification-based disambiguation setting). The transformation may include, for example, applying an input-to-tool-motion scale (also referred to as a master-slave scale), applying a filter, and identifying a characteristic motion type associated with a particular event. In various embodiments, the transformation may not affect the performance of the operator's commanded motion and may not be discernible to naked human eyes, but may be observable in the image data (e.g., by using image processing algorithms).

The method 800 is illustrated in FIG. 8 as a set of operations or processes 802 through 812. Not all of the illustrated processes 802 through 812 may be performed in all embodiments of method 800. Additionally, one or more processes that are not expressly illustrated in FIG. 8 may be included before, after, in between, or as part of the processes 802 through 812. In some embodiments, one or more of the processes may be implemented, at least in part, in the form of executable code stored on non-transitory, tangible, machine-readable media that, when run by one or more processors (e.g., the processors of a control system such as control system 20), causes the one or more processors to perform one or more of the processes.

The method 800 begins at process 802, where a control system may provide a first transformation-based disambiguation setting associated with a first tool controlled by a first manipulator. The first transformation-based disambiguation setting may provide a first predefined transformation to a first operator's commanded motion associated with the first tool. The control system may further provide a second transformation-based disambiguation setting associated with a second tool controlled by a second manipulator. The second transformation-based disambiguation setting may provide a second predefined transformation to a second operator's commanded motion associated with the second tool. The second predefined transformation may be different from the first transformation. In some embodiments, the first and second predefined transformations have different types (e.g., a master-slave scale transformation and a filter transformation respectively). In alternative embodiments, the first and second predefined transformations have the same type but different transformation amounts. For example, the first and second predefined transformations are both master-slave scale transformations but provide different scale values. For further example, the first and second predefined transformations are both filter transformations, but provide different cut-off frequencies or filters having different orders. Such differences may be used by the control system to establish the correspondences between the image-space tools and the first and second tools respectively.

In some embodiments, the method 800 may then proceed to process 804, where the first predefined transformation includes a first master-slave scale. In those embodiments, at process 804, the control system may apply the first master-slave scale to a first operator's commanded motion to control the first tool. In an example, the first master-slave scale has a value of 1:3, where the operator uses a first input device (e.g. a left-hand input control device 36-1 of FIG. 2) to control the first tool. In some embodiments, at process 804, the control system may apply a second master-slave scale of the second predefined transformation to a second operator's commanded motion to control the second tool. In an example, the second master-slave scale has a value (e.g., 1:3.1) that is different from the first master-slave scale (e.g., 1:3), where the operator uses a second input device (e.g. a right-hand input control device 36-2 of FIG. 2) to control the second tool.

The method 800 may proceed to process 806, where the control system performs image analysis algorithms to the image data and generate observed master-slave scales for all possible master-slave pairs. In an example where there are two image-space tools, for a particular input device, there may be two possible pairs, including a first possible pair including the particular input device and a first image-space tool and a second possible pair including the particular input device and a second image-space tool. In an example, the image analysis algorithms include a tool tracking algorithm that may compute distances travelled by the first image-space tool and second image-space tool, which may then be used to compute the observed master-slave scales for all possible master-slave pairs.

The method 800 may proceed to process 808, where the control system establishes correspondences between image-space tools and first and second tools based on the predefined transformations and observed possible transformations. For example, for the first tool controlled by a first input device, the control system determines that the observed master-slave scale of a possible pair including the first input device and the second image-space tool is the closest to the predefined first master-slave scale of the first predefined transformation, and establishes a correspondence between the second image-space tool and the first tool. For further example, for the second tool controlled by a second input device, the control system determines that the observed master-slave scale of a possible pair including the second input device and the first image-space tool is the closest to the predefined second master-slave scale of the second predefined transformation, and establishes a correspondence between the first image-space tool and the second tool.

Alternatively, in some embodiments, after process 802, the method 800 may proceed to process 810, where the first predefined transformation includes a first filter. In those embodiments, at process 810, the control system may apply the first filter to a first operator's commanded motion to control the first tool. The first filter may include one or more filter parameters including, for example, a first cut-off frequency, a first phase shift, a first notch frequency, a first resonant frequency, a first roll-off slope (e.g., based on an order of the first filter). In an example, the first filter is a low pass filter having a first cutoff frequency of 7 Hz. In some embodiments, at process 810, the control system may apply a second filter of the second predefined transformation to a second operator's commanded motion to control the second tool. The second filter may include one or more filter parameters including, for example, a second cut-off frequency, a second phase shift, a second north frequency, a second resonant frequency, a second roll-off slope (e.g., based on an order of the second filter). In various examples, the one or more filter parameters of the second filter may have different values from the corresponding one or more filter parameters of the first filter. In an example, the second filter is a low pass filter having a second cut off frequency of 7.5 Hz.

The method 800 may proceed to process 812, where the control system processes the image data to generate first observed filter parameter and second observed filter parameter for the image-space tools. In an example, for a particular image-space tool, the control system performs a Fast Fourier Transform (FFT) for the observed motion of that particular image-space tool along a single axis to generate spectral power in the frequency domain, and determines the filter parameters (e.g., a cut-off frequency, a phase shift, a north frequency, a resonant frequency, a roll-off slope) using the spectral power distribution in the frequency domain. In some embodiments, a transfer function is computed between each combination of a master input device and a tool motion estimate (e.g., for disambiguation using a scale).

The method 800 may proceed to process 808, where the control system establishes correspondences between image-space tools and first and second tools based on the predefined transformations (e.g., predefined cut-off frequency) and observed transformations (e.g., observed cut-off frequency). For example, for the first tool, the control system determines that the observed cut-off frequency of a first image-space tool is the closest to the predefined cut-off frequency of the first predefined transformation, and establishes a correspondence between the first image-space tool and the first tool. For example, for the second tool, the control system determines that the observed cut-off frequency of a second image-space tool is the closest to the predefined cut-off frequency of the second predefined transformation, and establishes a correspondence between the second image-space tool and the second tool.

In another alternative embodiment, after process 802, the method 800 may proceed to process 814, where the control system determines a first event associated with a first tool. An example of the first event is a tool engagement event where a first tool is engaged in a first manipulator and inserted into the patient. In various embodiments, the control system may determine the first event using sensor data from a sensor system (e.g., a tool tracking system with a camera external to the patient), kinematics data from the first manipulator coupled to the first tool, historical tool state (e.g., motion, pose) data, or a combination thereof. In some embodiments, the control system may determine the first event by using the tool tracking system to track one or more predefined features on the first tool.

The method 800 may proceed to process 816, where the control system may determine a first predefined motion characteristic associated with the first event based on the first transformation-based disambiguation setting. For example, the first transformation-based disambiguation setting associated with the first tool may provide that during a tool engagement event, the motion of the first tool has a first predefined motion characteristic (e.g., a largely linear movement).

The method 800 may proceed to process 818, where the control system processes the image data from the imaging device using image processing algorithms to generate observed motion characteristics for the image-space tools respectively. In an example, the control system generates a first observed motion characteristic of a first image-space tool including a linear movement, and a second observed motion characteristic of a second image-space tool including a stillness of a second image-space tool.

The method 800 may proceed to process 808, where the control system establishes correspondences between image-space tools and first and second tools based on the predefined transformations (e.g., a predefined motion characteristic associated with particular events) and observed transformations (e.g., an observed motion characteristic). For example, for the first tool, the control system determines that the observed motion characteristic (e.g., linear movement) of the first image-space tool matches the predefined motion characteristic (e.g., linear movement) associated with a first event (e.g., a tool engagement event) of the first tool, and establishes a correspondence between the first image-space tool and the first tool. A second correspondence between an image-space tool and the second tool may be determined substantially the same based on a second transformation-based disambiguation setting associated with the second tool.

Referring to FIG. 9, illustrated is a pose-estimate-based disambiguation method 900 (e.g., pose-based disambiguation process 510 of FIG. 5), where the disambiguation utilizes a pose-based disambiguation setting. In method 900, a control system generates a pose estimate of one or more portions of a tool based on information of the associated manipulator/input device, including, for example, sensor information provided by a sensor system, kinematics information of the associated manipulator/input device, or a combination thereof. The control system may establish the correspondence between the tool and an image-space tool based on the pose estimate and an observed pose of the corresponding one or more portions of the image-space tool using the image data. The pose estimate may comprise parameters sufficient to describe a full pose of the relevant portion(s) of the tool. The pose estimate may alternatively comprise fewer parameters and describe a partial pose of the relevant portion(s) of the tool, such as describing only the position, describing only the orientation, or describing both the position and orientation but to less than a full pose. The observed poses of the portion(s) of the image-space tool may be determined through any appropriate manner, including through the use of artificial intelligence—such as via machine learning systems or neural networks trained with appropriate training data sets.

In some embodiments, the pose estimate is of a portion of the tool, such as of a shaft, joint, or end effector of the tool. In some embodiments, the pose estimate is of a relative pose between two portions of the tool. In an example, the pose is an orientation of an end effector relative to the shaft. In another example with a jawed tool, the pose estimate includes a jaw pose (e.g., "jaws open," "jaws closed," a jaw opening amount) that is relative to two jaws of an end effector. A jaw opening amount may be expressed by any appropriate parameter or set of parameters, such as jaw opening size, jaw opening shape, jaw opening characteristic dimension such as opening angle, and the like. In those embodiments, by using a relative pose of two portions of the tool, the disambiguation process is improved compared to using a tool pose of a portion of the tool relative to the image, where the tool pose of the portion of the tool relative to the image may not be sufficient for disambiguation as it cannot be related to kinematic information in cases that base locations are unknown.

In some embodiments, the pose estimate describes relative poses among more than two portions of the tool. In an example, the pose estimate describes a first relative pose between the end effector and a wrist, and a second pose relative pose between the wrist and the tool shaft. As another example for a jawed tool, the pose estimate describes a jaw pose, and an orientation of the jaw relative to the shaft. In these embodiments, the control system may establish the correspondence between the tool and an image-space tool based on matching, using the image data, the multiple poses in the pose estimate with the observed poses of the corresponding portions of the image-space tool.

In an embodiment, the tool comprises jaws and a wrist, and the pose estimate comprises a simplified tool profile represented by a line model "tool skeleton". This simplified tool profile is formulated based on estimates of reference features of the tool, where these estimates are derived from known geometric dimensions of the tool and kinematic information. For example, these estimates may include estimates of the tips of the jaws of the tool, a clevis location, a center of the wrist, and a tool shaft axis. The control system utilizes a trained AI to identify in the image data corresponding portions of the image-space tool using the image data (e.g. the tips of the jaws of the tool, a clevis location, a center of the wrist, and a tool shaft axis). The control system then uses these identified image features to produce an observed simplified tool profile for matching to the pose estimate's simplified tool profile.

Figure 12:
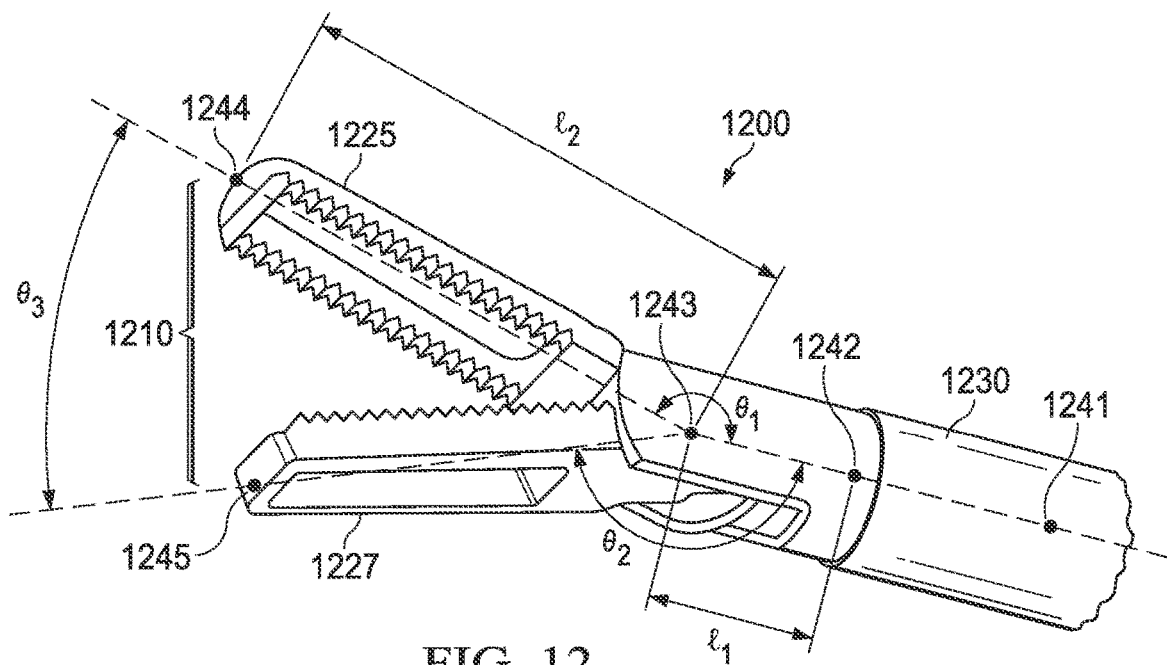
FIG. 12 illustrates example appearance and pose estimates for a tool, in accordance with an embodiment of the present disclosure.

FIG. 12 illustrates example appearance and pose estimates for a tool 1200, in accordance with an embodiment of the present disclosure. The tool 1200 includes a set of jaws comprising a first jaw 1225 and a second jaw 1227. The jaws 1225, 1127 are rotatably coupled to a clevis 1220, which couples the jaws 1225, 1227 to the shaft 1230. In various embodiments, the control system may determine any number of pose estimates for tool 1200, such as estimates for: the angle ($\theta_1$) between the first jaw 1225 and the shaft 1230, the angle ($\theta_2$) between the second jaw 1227 and the shaft 1230, or the amount of jaw opening. The amount of jaw opening can be characterized using any appropriate parameter, including a separation distance (d) between the jaws 1225, 1227, an angle ($\theta_3$) between the jaws 1225, 1227, and the like. In determining the pose estimates, the control system may identify landmark points on the tool 1200, such as a first shaft point 1241, a second shaft point 1242, a clevis point 1243, a first tip point 1244 for the first jaw 1225, and a second tip point 1245 for the second jaw 1227. The first and second shaft points may be defined based on particular features of the shaft, defined as located an offset distance from the clevis along the shaft direction, etc. In making the pose estimates, the control system can use such landmark points in isolation, or to define line segments, vector directions, or other geometric abstractions when in calculating distances, angles, or any other pose estimate parameter. FIG. 12 shows just one example of pose estimates, and other embodiments may involve fewer, more, or different pose estimates, landmark points, and the like. For example, a non-jawed tool would lack an amount of jaw opening, and may or may not have multiple points. As another example, in an embodiment the control system may define only the first shaft point 1241 and not the second shaft point 1242 (or vice versa). As yet another example, in another embodiment with a tool comprising multiple devises, the control system may define multiple clevis points, where each clevis point corresponds to a clevis.

To match the pose estimate with the corresponding one or more portions of the image-space tool using the image data, the control system may identify pairs of pose estimates and image-space tools that optimizes a least-squares fit or other criterion. As a specific example, a residual can be calculated for each permutation of pose estimate to image-space tool pair, and the set of pairs with the lowest residual is determined to be matched for disambiguation. Minimum or maximum thresholds may also be applied to require that matches meet particular requirements regarding error, residual, certainty, or the like.

The method 900 is illustrated in FIG. 9 as a set of operations or processes 902 through 908. Not all of the illustrated processes 902 through 908 may be performed in all embodiments of method 900. Additionally, one or more processes that are not expressly illustrated in FIG. 9 may be included before, after, in between, or as part of the processes 902 through 908. In some embodiments, one or more of the processes may be implemented, at least in part, in the form of executable code stored on non-transitory, tangible, machine-readable media that, when run by one or more processors (e.g., the processors of a control system such as control system 20), causes the one or more processors to perform one or more of the processes.

The method 900 begins at process 902, where a control system provides a first pose-estimate-based disambiguation setting associated with a first tool controlled by a first manipulator and/or a first master input device. The first pose-estimate-based disambiguation setting may include various disambiguation parameters, including, for example, manipulator/input device data source types, pose estimate types, etc. The manipulator/input device data source types may include, for example, sensor data, kinematics data, historical tool state (e.g., motion, pose) data, or a combination thereof for pose estimate. The first pose-estimate-based disambiguation setting may provide pose estimate types including, for example, an end effector pose estimate type (e.g. a tool tip pose estimate, a jaw pose estimate, a relative pose estimate of the end effector relative to a joint or a shaft or another part of the tool, etc.), a shaft pose estimate type (e.g. a shaft roll estimate, a relative pose estimate of the shaft relative to another part of the tool), a single degree of freedom pose estimate type of at least a portion of the tool, a wrist pose estimate (e.g. a bending estimate, a relative pose estimate of the wrist relative to another part of the tool), etc. In some embodiments, the jaw pose estimate type may correspond to a jaw degree of freedom classified into two or more states, including for example, "jaws open" or "jaws closed." In some embodiments, the jaw pose estimate type may provide that a jaw pose estimate includes a jaw opening amount estimate (e.g., using an angle between two jaws of an end effector). In an example, the single degree of freedom pose estimate type corresponds to one of the six degrees of freedom pose estimates including a forward/backward estimate, an up/down estimate, a left/right estimate, a yaw estimate, a pitch estimate, and a roll estimate. Such a single degree of freedom pose estimate type may provide a simpler disambiguation solution than using a full pose estimate (e.g. a six-degrees-of-freedom pose estimate).

The method 900 may proceed to process 904, where the control system generates a first pose estimate for the first tool or a portion thereof using sig manipulator/input device information (e.g., sensor data, kinematics data, historical tool state (e.g., motion, pose) data, or a combination thereof) information associated with the first manipulator that is coupled to the first tool. Such a first pose estimate may be generated based on the first pose-estimate-based disambiguation setting. For example, the manipulator information may include data having the manipulator data source types. The sensor system may include one or more sensors including, for example, an inertial measurement unit (IMU), an electromagnetic sensor, an optical tracking system, an image tracking system, a hybrid sensor system, encoders of the first manipulator, other suitable sensor systems, and a combination thereof. In an example, the image tracking system may include a camera external to the patient's anatomy and provide manipulator information (e.g., alignment information between the first manipulator and other manipulators and/or the patient, first manipulator movement information, etc.) using image tracking algorithms.

For further example, the first pose estimate may be generated according to the pose estimate types provided by the first pose-estimate-based disambiguation setting. The first pose estimate may include, for example, an end effector pose estimate, a wrist pose estimate, a shaft pose estimate, etc. Each of the pose estimates may have one or more degrees of freedom as provided by the first pose-estimate-based disambiguation setting.

In some embodiments, at process 904, the control system may generate a second pose estimate for a second tool or a portion thereof using manipulator/input device information (e.g., sensor data, kinematics data, historical tool state (e.g., motion, pose) data, or a combination thereof) associated with a second manipulator/second input device that is coupled to the second tool. The second pose estimate may be generated based on a second pose-estimate-based disambiguation setting associated with the second tool. In some embodiments, the first and second pose-estimate-based disambiguation settings include different the pose estimate types. In some embodiments, at process 904, each of the first and second pose estimates may include approximate locations of the tools in the field of view of the imaging device.

The method 900 may proceed to process 906, where the control system applies image processing algorithms to the image data from the imaging device, and generates a first observed pose associated with a first image-space tool and a second observed pose associated with a second image-space tool. In some embodiments, the first and second observed poses are generated based on the first and second pose-estimate-based disambiguation settings, each of the first and second observed poses may include observed pose data corresponding to the pose estimate types. In an example where the field of view of the imaging device is divided into regions (e.g., quadrants), each of the first and second observed pose information may include corresponding regions of the FOV where the image-space tools are located. Disambiguation may be possible using coarse position estimates where each image-space tool is located at a distinct region.

The method 900 may proceed to process 908, where the control system establishes a first correspondence between a first selected image-space tool and the first tool based on the first and second observed poses and the first pose estimate of the first tool. In some examples, the control system determines that an observed pose (e.g., an observed jaw opening amount) of a first selected image-space tool matches the first pose estimate (e.g., a jaw opening amount estimate), and establishes a correspondence between that first selected image-space tool and the first tool.

In some embodiments, at process 908, the control system establishes a second correspondence between a second selected image-space tool and the second tool based on the first and second observed poses and the second pose estimate of the second tool. In an example, the second selected image-space tool is chosen because it has an observed pose that matches the second pose estimate of the second tool. Those first and second correspondences may then be used in a registration to determine master-tool alignments for the first and second tools respectively, as discussed above with reference to process 516 of FIG. 5.

Referring to FIG. 10, illustrated is an appearance-based disambiguation method 1000 (e.g., appearance-based disambiguation process 512 of FIG. 5) where a control system may establish the correspondence between the tool and an image-space tool based on a predefined appearance provided by an appearance-based disambiguation setting and an observed appearance of the image-space tool using the image data. The method 1000 is illustrated in FIG. 10 as a set of operations or processes 1002 through 1006. Not all of the illustrated processes 1002 through 1006 may be performed in all embodiments of method 1000. Additionally, one or more processes that are not expressly illustrated in FIG. 10 may be included before, after, in between, or as part of the processes 1002 through 1006. In some embodiments, one or more of the processes may be implemented, at least in part, in the form of executable code stored on non-transitory, tangible, machine-readable media that, when run by one or more processors (e.g., the processors of a control system such as control system 20), causes the one or more processors to perform one or more of the processes.

The method 1000 begins at process 1002, where a control system provides a first appearance-based disambiguation setting associated with a first tool controlled by a first manipulator and a second appearance-based disambiguation setting associated with a second tool controlled by a second manipulator. The appearance-based disambiguation setting may provide a predefined appearance, including for example, an optically identifiable property of a tool or a portion of the tool. Examples of optically identifiable properties include: color; reflectiveness or transmissivity to visible, infrared, or ultraviolet light; geometric properties such as shapes or dimensions (e.g. width, length, size); number of degrees of freedom; types of degrees of freedom; number of joints; types of joints; translucency; surface pattern, textual or graphical markings; natural tool landmarks; artificial markers; any other presentation property; and/or a combination thereof. Example portions of tools include shafts, end effector, jaws for jawed tools, wrists for wristed tools, and any other parts of tools.

As an example, the appearance-based disambiguation setting comprises one or more dimensions based on geometric properties of the tool, such as the tip length, the end effector width, a distance between two joints of the tool, the shaft diameter, or some other tool dimension. The observed appearance of the image-space tool is determined through any appropriate manner, including through the use of artificial intelligence such as via machine learning systems or neural networks trained with appropriate training data sets to identify relevant shapes, colors, patterns, tool landmarks, etc. Dimensions such as area, length, width, circumference, distance, and the like can be determined through post-processing of the identified tool shapes and tool landmarks.

FIG. 12 illustrates example appearance and pose estimates for a tool 1200, in accordance with an embodiment of the present disclosure. In various embodiments, the control system may determine any number of geometric parameters for appearance-based disambiguation, such as estimates for: the length ($l_1$) between a defined location along the shaft (e.g., second shaft point 1242) and the clevis, the length ($l_2$) of the first jaw 1225, the length ($l_3$) of the second jaw 1227, etc. In determining the pose estimates, the control system may identify and use landmark points on the tool 1200. For example, in some embodiments, the control system calculates the distance to the clevis by using the clevis point 1243, calculates the length ($l_2$) of the first jaw 1225 as the distance between clevis point 1243 and the first tip point 1244, or calculates the length ($l_3$) of the first jaw 1227 as the distance between clevis point 1243 and the second tip point 1245. FIG. 12 shows just one example of geometric parameters for appearance-based disambiguation, and other embodiments may involve fewer, more, or different geometric parameters, landmark points, etc.

In a specific example, in an embodiment with a tool comprising a jaw and a wrist, the appearance-based disambiguation setting comprises geometric properties of the tool including tip length and clevis-to-wrist distance. The appearance-based disambiguation settings for the tools are derived from preprogrammed information. In an embodiment, the tool's geometric properties stored in a memory of the tool, and provided to the control system by the tool. In another embodiment, the geometric properties are stored in a memory of the control system; the tool conveys its model or specific identity to the control system, and the control system cross-references that model or specific identity to the applicable geometric properties for that tool.

In some embodiments, the predefined appearance may include a unique synthetic marker including identifying features. The marker may include an optical, machine-readable, representation of data. In an example, the marker may include a barcode, a Quick Response (QR) code. In another example, the marker may include an encoded tool serial number, which may be used to identify a particular tool among tools with the same tool styles in the field of view of the imaging device. In another example, the marker may be visible only in a light wavelength band (e.g., in a near infrared wavelength band, in a band outside of a visible spectrum (e.g., between about 390 nanometers to 700 nanometers) for a naked human eye. In yet another example, the marker includes spectral coding (e.g., using one of a reflectance, absorption, transmission, or fluorescence at a particular wavelength band). In yet another example, the marker may be active (e.g., by emitting light). In that example, the marker (e.g., located at a shaft or a tool tip of the tool) may emit light (e.g., using a light source (e.g., a light-emitting diode (LED)) integrated with the tool tip, a fiber optic, a light guide, etc.). The properties of the emitted light (e.g., color, wavelength, pulsed waveform) for this active marker may be used to identify the tool.

In some embodiments, such a predefined appearance may be distinct for a particular tool, which may be used to uniquely identify an image-space tool from a plurality of image-space tools to its corresponding tool. In some embodiments, the predefined appearance of a tool may be used to map the tool to a corresponding manipulator. In some embodiments, such a predefined appearance may be distinct for a particular tool, which may be used to uniquely identify an image-space tool from a plurality of image-space tools to its corresponding tool. In some embodiments, the predefined appearance of a tool may be used to map the tool to a corresponding manipulator. In an example, when a tool is engaged and/or attached to the manipulator, the control system may determine the predefined appearance of a tool using information from the tool outside of the image-space. For example, the predefined appearance of a tool can be provided directly or indirectly by the tool (e.g., directly encoded in information from a radio-frequency identification (RFID) tag, an electrical circuit, a memory, etc., or indirectly provided through tool identification information sufficient for the control system to cross reference the associated predefined appearance).

The method 1000 may then proceed to process 1004, where the control system processes image data from the imaging device to generate a first observed appearance associated with a first image-space tool and a second observed appearance associated with a second image-space tool. In some embodiments, the imaging device is a multi-spectral imaging device and may be used to capture image data for markers using spectral encoding. The control system may use various algorithms (e.g., image processing, decoding) to extract observed appearance information of the image-space tools, including for example, generating tool identification information from the markers.

The method 1000 may then proceed to process 1006, where the control system establishes a first correspondence between a first selected image-space tool and a first tool by matching the observed appearance of the first selected image-space tool and a predefined appearance of the first tool. Similarly, at process 1006, the control system may establish a first correspondence between a second selected image-space tool and a second tool by matching the observed appearance of the second selected image-space tool and a predefined appearance of the second tool.

Referring to FIG. 11, illustrated is an operator-specified disambiguation method 1000 (e.g., operator-specified disambiguation process 514 of FIG. 5) where a control system may establish the correspondence between the tool and an image-space tool based on an instructed operator input provided by an operator-specified disambiguation setting. The method 1100 is illustrated in FIG. 11 as a set of operations or processes 1102 through 1112. Not all of the illustrated processes 1102 through 1112 may be performed in all embodiments of method 1100. Additionally, one or more processes that are not expressly illustrated in FIG. 11 may be included before, after, in between, or as part of the processes 1102 through 1112. In some embodiments, one or more of the processes may be implemented, at least in part, in the form of executable code stored on non-transitory, tangible, machine-readable media that, when run by one or more processors (e.g., the processors of a control system such as control system 20), causes the one or more processors to perform one or more of the processes.

The method 1100 begins at process 1102, where a control system provides a first operator-specified disambiguation setting associated with a first tool controlled by a first manipulator. In some embodiments, at process 1102, the control system also provides a second operator-specified disambiguation setting associated with a second tool controlled by a second manipulator. Each of the first and second operator-specified disambiguation setting may provide a predefined operator operation including, for example, a target operator-commanded motion or a request for operator input on correspondences between image-space tools and first/second tools.

In some embodiments, the method 1100 proceeds to process 1104, where a control system may provide instructions (e.g., using a display, an audio instruction) to the operator to move a particular tool (e.g., using a left-hand master input device or a right-hand master input device) with a target motion (e.g., with a target motion type, a target motion amount) or a target pose (e.g., with one or more degrees of freedom). The control system may also provide instructions to the operator to keep the other tools stationary. The method 1100 may proceed to process 1106, where the control system processes the image data from the imaging device to generate observed motions/poses associated with the image-space tools. The method 1100 may then proceed to process 1108, where the control system establishes correspondences between a first selected image-space tool and the first tool by matching the observed motion/pose of the first selected image-space tool and the instructed target motion/pose for the first tool.

Alternatively, in some embodiments, after process 1102, the method 1100 may proceed to process 1110, where the control system may instruct the operator to provide an input to identify corresponding image-space tools in a display to the corresponding tools. In an example, the operator may use a graphical cursor to hover over and click each image-space tool and its correspondence with the tool. Such identification may be performed by the operator by identifying a hand (e.g., a left hand or a right hand), a manipulator (e.g., with a particular location), or an operator (e.g., with a particular location). In another example, the operator may provide such inputs using a touch screen of the operator console. The method 1100 may then proceed to process 1112, where the control system establishes the correspondences between the image-space tools and the first tool based on the operator input.

In various embodiments, the disambiguation process may be performed before or during an operation (e.g., a medical operation). In a medical example, the disambiguation process may be performed before the medical operation (e.g. during set-up) outside of the patient or inside the patient. In another example, the disambiguation process may be performed during the medical operation. In yet another example, the disambiguation process may be used in a robotic system having manipulators on the same base to check and confirm registration of those manipulators with their respective tools. In some embodiments, a combination of the disambiguation processes (e.g., processes 600, 700, 800, 900, 1000, 1100) may be performed to provide improved accuracy, robustness, and redundancy. For example, such a combination of met disambiguation processes may be used when some tools (e.g., the imaging tool and tools in the FOV of the imaging tool) are robotically controlled and other tools are manually controlled. In some embodiments, a disambiguation process may be performed once to establish the correspondences between the image-space tools and the tools, and such correspondences are tracked over time. In some embodiments, one or more disambiguation processes may be performed when the control system determines events that may increase ambiguity. Such events may include, for example, replacing the imaging device of the imaging tool 15, replacing the tools, system re-docking, etc.

In various embodiments, the disambiguation process may be used in various applications in surgical and non-surgical robotic systems, and in medical and non-medical robotic systems (e.g., industrial and recreational robotic systems). While registration in surgical robotic systems is used as an example of such an application using the disambiguation process, the disambiguation process may be used in various other applications in surgical and non-surgical robotic systems, and in medical and non-medical robotic systems. In an example, the disambiguation process is used in a graphical information display system of a robotic system, which provides an overlay of graphical information about a particular manipulator, its tool, or its input device on top of the image of the corresponding tool in a display. The graphical information may include manipulator information (e.g. manipulator status, manipulator motions or speed) and tool information (e.g., tool status and characteristics). The graphical information may also include special functions commanded of the end effector (e.g., such as suction or irrigation for suction irrigator, command to clamp or cut for stapler, application of energy for electrocautery or ultrasonic or some other energy, etc.), hand mapping information, control functionality availability from operator inputs, quality of registration, range of motion information for the tool or the input device, recommendations for alternative tools, interface for sharing/exchanging tools between multiple operators, scene annotation, and measurement of the tools, training and guidance information, etc. In yet another example, the disambiguation process is used in providing guidance to an assistant by being able to indicate (e.g., on a display, on each manipulator, or in a wearable augmented reality headset) the tool and manipulator mappings. For example, upon receiving an operator's instruction (e.g., "please remove the instrument in my left hand", "please remove the grasper on the right of the screen"), the tool and manipulator mappings provided by the disambiguation process aids the assistant in moving a corresponding manipulator as instructed by the operator. In yet another example, the disambiguation process is used in applications related to autonomous task execution, visual servoing of tools (e.g., by using a vision-based tracking feedback signal for control), or coordination of multiple tools using machine vision information. In those examples, the disambiguation process may include the mapping from the image space to the manipulator space.

One or more elements in embodiments of the invention may be implemented in software to execute on a processor of a computer system such as control processing system. When implemented in software, the elements of the embodiments of the invention are essentially the code segments to perform the necessary tasks. The program or code segments can be stored in a processor-readable storage medium or device that may have been downloaded by way of a computer data signal embodied in a carrier wave over a transmission medium or a communication link. The processor readable storage device may include any medium that can store information including an optical medium, semiconductor medium, and magnetic medium. Processor readable storage device examples include an electronic circuit; a semiconductor device, a semiconductor memory device, a read-only memory (ROM), a flash memory, an erasable programmable read-only memory (EPROM); a floppy diskette, a CD-ROM, an optical disk, a hard disk, or other storage device. The code segments may be downloaded via computer networks such as the Internet, Intranet, etc.

Note that the processes and displays presented may not inherently be related to any particular computer or other apparatus. Various general-purpose systems may be used with programs in accordance with the teachings herein, or it may prove convenient to construct a more specialized apparatus to perform the operations described. The required structure for a variety of these systems will appear as elements in the claims. In addition, the embodiments of the invention are not described with reference to any particular programming language. It will be appreciated that a variety of programming languages may be used to implement the teachings of the invention as described herein.

While certain exemplary embodiments of the invention have been described and shown in the accompanying drawings, it is to be understood that such embodiments are merely illustrative of and not restrictive on the broad invention, and that the embodiments of the invention not be limited to the specific constructions and arrangements shown and described, since various other modifications may occur to those ordinarily skilled in the art.

What is claimed is:

1. A robotic system comprising:
   a plurality of manipulators; and
   a control system communicatively coupled to the plurality of manipulators, the control system configured to:
      receive image data provided by an imaging device, the image data being of a plurality of tools, the plurality of tools physically coupled to the plurality of manipulators,
      determine, based on the image data, a plurality of image-space tools, each image-space tool associated with a tool of the plurality of tools,
      determine a first correspondence of a first image-space tool of the plurality of image-space tools with a first tool of the plurality of tools based on a first tool correspondence setting associated with the first tool, and
      control the first tool by:
         identifying a first manipulator of the plurality of manipulators as coupled to the first tool;
         determining, based at least on the first correspondence, a first alignment relationship between the imaging device and the first tool;
         calculating, based at least on the first alignment relationship, motion of the first manipulator to move the first tool in accordance with a movement command; and
         commanding movement of the first manipulator based on the calculated motion.

2. The robotic system of claim 1, further comprising an input device communicatively coupled to the control system, wherein the control system is further configured to:
   receive, from the input device, the movement command.

3. The robotic system of claim 1, wherein the control system determines the first correspondence when the first tool is coupled to the first manipulator of the plurality of manipulators and receives the image data when the imaging device is coupled to a second manipulator of the plurality of manipulators,
   wherein the first manipulator has a first base, and
   wherein the second manipulator has a second base physically independent from the first base.

4. The robotic system of claim 1, wherein the control system is further configured to determine a second correspondence between a second image-space tool of the plurality of image-space tools and a second tool of the plurality of tools based on a second tool correspondence setting associated with the second tool,
   wherein each of the first and second tool correspondence settings is of a type selected from the group consisting of a pose-based setting, an operator-specified setting, an appearance-based setting, and a motion-based setting, and
   wherein the first and second tool correspondence settings are of different types.

5. The robotic system of claim 1, wherein the first tool correspondence setting includes an operator-specified setting, and wherein the control system is further configured to:
   instruct an operator to move the first tool with a first movement; and
   determine the first correspondence based on a performance of the first movement.

6. The robotic system of claim 1, wherein the first tool correspondence setting includes an appearance-based setting.

7. The robotic system of claim 6, wherein the appearance-based setting includes a visual feature of the first tool.

8. The robotic system of claim 7, wherein the visual feature includes a first marker on the first tool or a dimensional feature of the first tool.

9. The robotic system of claim 1, wherein the first tool correspondence setting includes a pose-based setting.

10. The robotic system of claim 1, wherein the control system is further configured to:
    determine a first pose estimate of the first tool using manipulator data of the first manipulator of the plurality of manipulators when the first manipulator is physically coupled to the first tool; and
    determine the first correspondence based on the first pose estimate.

11. The robotic system of claim 10, wherein the first pose estimate includes an end effector pose estimate of an end effector of the first tool, and
    wherein the end effector pose estimate includes an estimate of:
       an amount of opening of two jaws of the end effector; or
       a relative pose of the end effector relative to another portion of the first tool.

12. The robotic system of claim 10, wherein the first pose estimate includes:
- a rotation amount estimate of the first tool about a first axis of the first tool; or
- a shaft pose estimate of a shaft of the first tool; or
- a wrist pose estimate of a wrist of the first tool; or
- a plurality of poses of a plurality of portions of the first tool.

13. The robotic system of claim 1, wherein the first tool correspondence setting includes a first motion-based setting.

14. The robotic system of claim 1, wherein the control system is further configured to:
- control the first manipulator coupled to the first tool based on a first modification of a first operator-commanded motion based on a modification-based setting; and
- determine the first correspondence based on the first modification.

15. A method performed by a computing system, the method comprising:
- receiving image data provided by an imaging device, the image data being of a plurality of tools, the plurality of tools physically coupled to a plurality of manipulators,
- determining, based on the image data, a plurality of image-space tools, each image-space tool associated with a tool of the plurality of tools,
- determining a first correspondence of a first image-space tool of the plurality of image-space tools with a first tool of the plurality of tools based on a first tool correspondence setting associated with the first tool, and
- controlling the first tool by:
  - identifying a first manipulator of the plurality of manipulators as coupled to the first tool;
  - determining, based at least on the first correspondence, a first alignment relationship between the imaging device and the first tool;
  - calculating, based at least on the first alignment relationship, motion of the first manipulator to move the first tool in accordance with a movement command; and
  - commanding movement of the first manipulator based on the calculated motion.

16. The method of claim 15, further comprising:
- instructing an operator to move the first tool with a first movement; and
- receiving, from the operator, the first tool correspondence setting based on a performance of the first movement.

17. The method of claim 15, wherein the first tool correspondence setting includes an appearance-based setting.

18. The method of claim 15, wherein the first tool correspondence setting includes a pose-based setting.

19. The method of claim 15, wherein the first tool correspondence setting includes a motion-based setting.

20. A non-transitory machine-readable medium comprising a plurality of machine-readable instructions which, when executed by one or more processors, are adapted to cause the one or more processors to perform a method comprising:
- receiving image data provided by an imaging device, the image data being of a plurality of tools, the plurality of tools physically coupled to a plurality of manipulators,
- determining, based on the image data, a plurality of image-space tools, each image-space tool associated with a tool of the plurality of tools,
- determining a first correspondence of a first image-space tool of the plurality of image-space tools with a first tool of the plurality of tools based on a first tool correspondence setting associated with the first tool, and
- controlling the first tool by:
  - identifying a first manipulator of the plurality of manipulators as coupled to the first tool;
  - determining, based at least on the first correspondence, a first alignment relationship between the imaging device and the first tool;
  - calculating, based at least on the first alignment relationship, motion of the first manipulator to move the first tool in accordance with a movement command; and
  - commanding movement of the first manipulator based on the calculated motion.

* * * * *

UNITED STATES PATENT AND TRADEMARK OFFICE
CERTIFICATE OF CORRECTION

| | | |
|---|---|---|
| PATENT NO. | : 12,162,143 B2 | Page 1 of 1 |
| APPLICATION NO. | : 18/409350 | |
| DATED | : December 10, 2024 | |
| INVENTOR(S) | : Simon P. Dimaio et al. | |

It is certified that error appears in the above-identified patent and that said Letters Patent is hereby corrected as shown below:

In the Specification

Column 24, Line 38, change "devises" to -- clevises --

Signed and Sealed this
Eleventh Day of February, 2025

Coke Morgan Stewart
*Acting Director of the United States Patent and Trademark Office*